United States Patent [19]
Hofer et al.

[11] 3,966,730
[45] June 29, 1976

[54] PYRIMIDIN(4)-YL-(THIONO)-(THIOL)-PHOSPHORIC-(PHOSPHONIC)-ACID ESTERS

[75] Inventors: Wolfgang Hofer; Fritz Maurer; Hans-Jochem Riebel; Lother Rohe, all of Wuppertal; Wolfgang Behrenz, Overath-Steinenbruck; Ingeborg Hammann, Cologne; Wilhelm Stendel, Wuppertal; Bernhard Homeyer, Opladen, all of Germany

[73] Assignee: Bayer Aktiengesellschaft, Leverkusen, Germany

[22] Filed: Aug. 22, 1974

[21] Appl. No.: 499,808

[30] Foreign Application Priority Data
Aug. 31, 1973 Germany............................ 2343931

[52] U.S. Cl. ....................... 260/251 P; 260/251 A; 260/251 R; 260/256.4 E; 260/256.5 R; 424/200
[51] Int. Cl.² ............................................. C07F 9/65
[58] Field of Search................................ 260/251 P

[56] References Cited
UNITED STATES PATENTS

| | | | |
|---|---|---|---|
| 3,862,188 | 1/1975 | Milzner et al. .................. | 260/251 P |
| 3,886,156 | 5/1975 | Hofer et al. ..................... | 260/251 P |

FOREIGN PATENTS OR APPLICATIONS

| | | | |
|---|---|---|---|
| 1,140,580 | 12/1962 | Germany.......................... | 260/251 P |
| 1,193,055 | 5/1965 | Germany.......................... | 260/251 P |

OTHER PUBLICATIONS

Reznik et al. Chemical Abstracts, vol. 79, 42,445K, 8/20/73.

Primary Examiner—Raymond V. Rush
Assistant Examiner—Diana G. Rivers
Attorney, Agent, or Firm—Burgess, Dinklage & Sprung

[57] ABSTRACT

Pyrimidin(4)-yl-(thiono)-phosphoric-(phosphonic) acid esters and ester amides of the formula

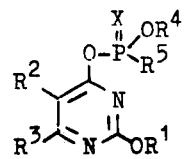

in which
R¹ is hydrogen, alkyl, cycloalkyl, alkenyl, alkynyl, aryl or aralkyl,
R² is hydrogen, alkyl, alkoxy, alkylmercapto, alkylcarbonyl, alkoxycarbonyl, halogen, nitrile or thiocyanato,
R³ is hydrogen, alkyl, aryl or alkoxycarbonylalkyl, or
R² is R³ conjointly form an alkylene bridge which forms a 5-membered to 7-membered ring with the adjoining carbon atoms,
R⁴ is alkyl or alkoxyalkyl,
R⁵ is alkyl, alkoxy, alkylmercapto, alkylamino, or aryl, and
X is oxygen or sulfur,
which possess insecticidal, acaricidal and nematocidal properties.

3 Claims, No Drawings

PYRIMIDIN(4)-YL-(THIONO)-(THIOL)-PHOSPHORIC-(PHOSPHONIC)-ACID ESTERS

The present invention relates to and has for its objects the provision of particular new pyrimidin(4)-yl-(thiono)-(thiol)-phosphoric(phosphonic) acid esters and ester amides which on the pyrimidine ring carry a hydroxy or ether group in the 2-position, are optionally substituted in the 5- and 6-positions and which are esterified in the 4-position, which possess insecticidal, acaricidal or nematocidal properties, active compositions in the form of mixtures of such compounds with solid and liquid dispersible carrier vehicles, and methods for producing such compounds and for using such compounds in a new way especially for combating pests, e.g. insects, acarids and nematodes with other and further objects becoming apparent from a study of the within specification and accompanying examples.

It is known from Swiss Pat. No. 321,868 and German Pat. No. 910,652 that O,O-diethyl-O-[2-isopropylmercapto- (Compound A) and 2-methylmercapto-6-methyl-pyrimidyl-(4)]- (Compound B) and O,O-diethyl-O-[2-isopropyl-6-methylpyrimidyl-(4)]-thionophosphoric acid esters (Compound C) exhibit insecticidal and acaricidal properties.

The present invention now provides, as new compounds, the pyrimidin(4)-yl-(thiono)-(thiol)-phosphoric-(phosphonic) acid esters and ester-amides of the general formula

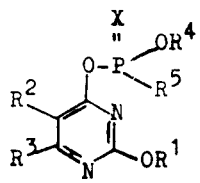

in which
$R^1$ is hydrogen, alkyl, cycloalkyl, alkenyl, alkynyl, aryl or aralkyl,
$R^2$ is hydrogen, alkyl, alkoxy, alkylmercapto, alkylcarbonyl, alkoxycarbonyl, halogen, nitrile or thiocyanato,
$R^3$ is hydrogen, alkyl, aryl or alkoxycarbonylalkyl, or $R^2$ and $R^3$ conjointly from an alkylene bridge which forms a 5-membered to 7-membered ring with the adjoining carbon atoms,
$R^4$ is alkyl or alkoxyalkyl,
$R^5$ is alkyl, alkoxy, alkylmercapto, alkylamino, or aryl, and
X is oxygen or sulfur.

Preferably $R^1$ is straight-chain or branched alkyl with 1 to 20, especially 1 to 12, carbon atoms, cycloalkyl with 5 to 7, especially 6, carbon atoms, alkenyl or alkynyl with 2 to 6, especially 3 to 6, carbon atoms, aryl with 6 to 10, especially 6, carbon atoms or aralkyl with 6 to 10, especially 6, carbon atoms in the aryl moiety and 1 or 2 carbon atoms in the alkyl moiety; $R^2$ is hydrogen, straightchain or branched lower alkyl with 1 to 4, especially 1 or 2, carbon atoms, lower alkoxy with 1 to 4, preferably 1 or 2, carbon atoms, lower alkylmercapto with 1 to 4, especially 1 or 2, carbon atoms, lower alkylcarbonyl or alkoxycarbonyl with 1 to 4, especially 1 or 2, carbon atoms in the alkyl or alkoxy moiety, halogen, especially chlorine or bromine, or nitrile; $R^3$ is hydrogen, straight-chain or branched alkyl with 1 to 6, especially 1 to 4, carbon atoms, aryl with 6 to 10, especially 6, carbon atoms, or lower alkoxycarbonyllower alkyl with 1 to 4 carbon atoms in the alkoxy radical and 1 to 2 carbon atoms in the alkyl radical; or $R^2$ and $R^3$ conjointly form an alkylene bridge with 3 to 5 members which forms a cyclopentyl, cyclohexyl or cycloheptyl ring with the two adjoining carbon atoms; $R^4$ is straight-chain or branched alkyl with 1 to 12, especially 1 to 9, carbon atoms, alkoxyalkyl with 1 to 12, especially 1 to 9, carbon atoms in the alkyl part and 1 to 4 carbon atoms in the alkoxy part; and $R^5$ to straight-chain or branched alkyl, alkoxy or alkylmercapto with 1 to 6, especially 1 to 4, carbon atoms, alkylamino with 1 to 6, especially 1 to 4, carbon atoms or aryl with 6 to 10, especially 6, carbon atoms.

Surprisingly, the pyrimidin(4)-yl-(thio)phosphoric acid esters and ester-amides and -phosphonic acid esters and ester-amides according to the invention are distinguished by a substantially greater insecticidal and acaricidal action than the known O,O-diethyl-O-[2-isopropylmercapto- or 2-methylmercapto-6-methyl-pyrimidyl-(4)]- and O,O-diethyl-O-[2-isopropyl-4-methyl-pyrimidyl(4)]-thionophosphoric acid esters of analogous structure and of the same type of action. Compounds of the formula (I) also have a nematocidal action. The compounds according to the invention thus represent a genuine enrichment of the art.

The present invention also provides a process for the preparation of a pyrimidin(4)-yl-(thiono)-(thiol)-phosphoric-(phosphonic) acid ester or ester-amide of the formula (I), in which a 4-hydroxy-pyrimidine, or its sodium or potassium salt, of the general formula

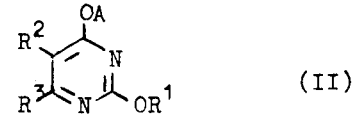

in which $R^1$, $R^2$ and $R^3$ have the above-mentioned meanings, and
A is hydrogen or a sodium or potassium ion, is reacted with a (thio)phosphoric or (thio)phosphonic acid halide of the general formula

in which
$R^4$, $R^5$ and X have the above-mentioned meanings, and Hal is halogen, optionally in the presence of an acid-binding agent and optionally in the presence of a solvent or diluent.

Hal in formula (III) is preferably chlorine or bromine, chlorine being especially preferred.

If 2-methoxy-4-hydroxy-6-methyl-pyrimidine and O,O-diethylthiono-phosphoric acid ester chloride are used as starting compounds, the course of the reaction can be represented by the following equation:

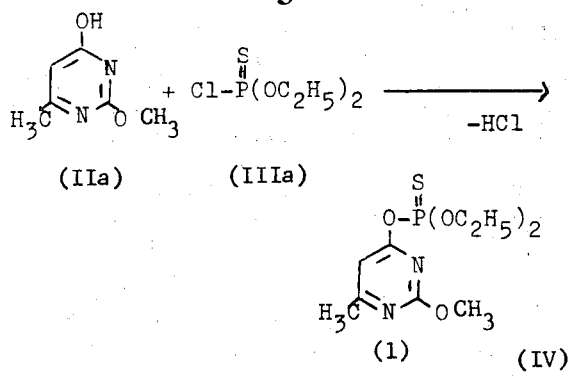

The 4-hydroxy-pyrimidines of the formula (II), which can be used according to the invention have in most cases not yet been described in the literature, but can be prepared according to a process which is known in principle, by reacting isoureas (see Houben-Weyl "Methoden der organischen Chemie" ("Methods of Organic Chemistry"). Georg Thieme Verlag Stuttgart, 1952, volume 8, page 170) with β-carbonyl-carboxylic acid esters (see Journal of the American Chemical Society, volume 26 (1904), page 454, "Reaction of Acetoacetic Esters with O-methylisourea and O-ethylisourea") or their enol ethers, in accordance with the following equation:

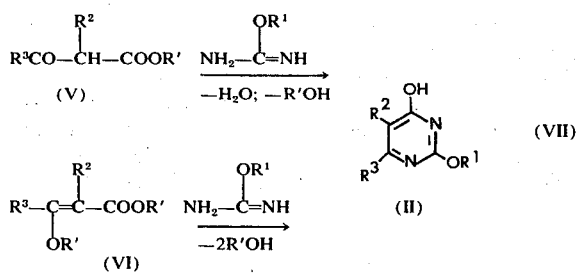

Instead of the free isoureas, their hydrochlorides can also be used, with addition of a suitable acid-binding agent.

The following may be mentioned as examples of pyrimidines of the formula (II): 4-hydroxy-2-methoxy-6-methyl-pyrimidine, 4-hydroxy-2-methoxy-6-methoxycarbonylmethyl-pyrimidine, 5-acetyl-4-hydroxy-2-methoxy-pyrimidine, 5-bromo-4-hydroxy-2-methoxy-6-methyl-pyrimidine, 5-chloro-4-hydroxy-2-methoxy-6-methyl-pyrimidine, 5,6-dimethyl-4-hydroxy-2-methoxy-pyrimidine, 5-ethyl-4-hydroxy-2-methoxy-6-methyl-pyrimidine, 2-methoxy-4-hydroxy-6-methyl-5-methylmercapto-pyrimidine, 2,5-diethoxy-4-hydroxy-pyrimidine, 2-ethoxy-4-hydroxy-5-ethoxycarbonyl-pyrimidine, 4-hydroxy-2-isopropoxy-6-methyl-pyrimidine, 4-hydroxy-2-isopropoxy-6-phenyl-pyrimidine, 4-hydroxy-2-isopropoxy-6-methoxy-carbonylmethyl-pyrimidine, 5-acetyl-4-hydroxy-2-isopropoxy-pyrimidine, 5-bromo-4-hydroxy-2-isopropoxy-6-methyl-pyrimidine, 5-chloro-4-hydroxy-2-isopropoxy-6-methyl-pyrimidine, 5,6-dimethyl-4-hydroxy-2-isopropoxy-pyrimidine, 2-cyclohexyloxy-4-hydroxy-6-methyl-pyrimidine, 2-cyclohexyloxy-4-hydroxy-5,6-trimethylene-pyrimidine, 5-chloro-2-cyclohexyloxy-4-hydroxy-6-methylpyrimidine, 2-ethoxy-4-hydroxy-6-methyl-pyrimidine, 2-dodecyloxy-4-hydroxy-6-methyl-pyrimidine, 2-allyloxy-4-hydroxy-6-methyl-pyrimidine and 4-hydroxy-6-methyl-2-propargyloxy-pyrimidine.

The (thio)phosphoric(phosphonic) acid halides of the formula (III) to be used in accordance with the process are known from the literature.

The following may be mentioned as examples thereof: O,O-dimethyl-, O,O-diethyl-, O,O-di-n-propyl-, O,O-di-isopropyl-, O,O-di-n-butyl-, O,O-di-isobutyl-, O,O-di-sec.-butyl- and O,O-di-tert.-butyl-phosphoric acid ester chlorides and the corresponding thiono analogues; O-ethyl-, O-n-propyl-, O-isopropyl-, O-n-butyl-, O-isobutyl-, O-sec.-butyl, O-tert.-butyl-, O-n-pentyl-, O-n-hexyl-, O-n-heptyl-, O-n-octyl-, O-n-nonyl-O-methyl- and -O-ethyl-phosphoric acid ester chlorides and the corresponding thiono analogues; O-methyl-, O-ethyl-, O-n-propyl, O-isopropyl-, O-n-butyl-, O-sec.-butyl-, O-isobutyl- and O-tert.-butyl-methane-, -ethane-, -n-propane-, isopropane-, -butane- and -benzene-phosphonic acid ester chlorides and the corresponding thiono analogues; O-methyl-, O-ethyl-, O-n-propyl-, O-isopropyl-, O-n-butyl-, O-iso-butyl-, O-sec.-butyl- and O-tert.-butyl-N-methyl-, -N-ethyl-, -N-n-propyl- and -N-iso-propyl-phosphoric acid ester-amide chlorides and the corresponding thiono analogues; and O,S-dimethyl-, O,S-diethyl-, O,S-di-n-propyl-, O,S-diisopropyl-, O,S-di-n-butyl-, O,S-di-isobutyl-, O,S-di-sec.-butyl-, O,S-di-tert.-butyl-, O-methyl-S-ethyl-, O-ethyl-S-methyl-, O-ethyl-S-n-propyl- and O-ethyl-S-isopropylthiolphosphoric acid ester chlorides and the corresponding thiono analogues.

The process for the preparation of the new compounds (I) is preferably carried out with conjoint use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; nitriles, for example acetonitrile and propionitrile; and amides such as dimethylformamide.

All customary acid-binding agents can be used as acid acceptors. Compounds which have provided particularly suitable are alkali metal carbonates and alkali metal alcoholates, such as sodium carbonate, methylate and ethylate and potassium carbonate, methylate, ethylate and tert.-butylate, and also aliphatic, aromatic or heterocyclic amines, for example triethylamine, trimethylamine, dimethylaniline, dimethylbenzylamine and pyridine.

The reaction temperatures can be varied within a fairly wide range. In general, the reaction is carried out at between 0° and 120°C, preferably at between 20° and 80°C.

The preparative process is preferably carried out under normal pressure.

To carry out the process, the starting compounds are in most cases employed in equimolar amounts. An excess of one or other reactant produces no significant advantages. The reaction is in general carried out in a suitable solvent, if appropriate in the presence of an acid acceptor, and the reaction mixture is then stirred for several hours. The mixture is then poured into water and worked up according to customary methods.

Water-soluble products are isolated by filtering the reaction mixture to remove any inorganic salt and distilling off the solvent under reduced pressure.

The new compounds are, in some cases, obtained in the form of oils which cannot be distilled without decomposition but can be freed of the last volatile constituents by socalled "slight distillation", that is to say prolonged heating under reduced pressure to moderately elevated temperatures, and can be purified in this way. They are characterized by their refractive indexes. Some of the products are obtained in a crystalline form; in that case, they can be characterized by their melting points.

As has already been mentioned, the pyrimidin(4)-yl-(thio)-(thiono)-phoshoric(phosphonic) acid esters and ester-amides according to the invention are distinguished by an outstanding insecticidal, acaricidal and nematocidal activity, especially against plant pests and pests harmful to health. They possess a good action both against sucking and biting insects and against mites (Acarina). For this reason, the compounds according to the invention can be employed successfully as pesticides in plant protection and in the hygiene and veterinary fields.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (Lymantria dispar), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (Prodenis litura), the ermine moth (*Hyponomeuta padella*), the Mediterranean flour moth (*Ephestia kühniella*) and greater wax moth (*Galleria mellonella*).

Also to be classed with the biting insects are beetles (coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarius*), the flour beetle (*Tribolium castaneum*), the northern corn billbug (Calandra or *Sitophilus zeamais*), *the drugstore beetle (Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (Fannia canicularis), the black blow fly (*Phormia aegina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the twospotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

As ectoparasites in animals there may be mentioned, from the class of the insects: Diptera larvae which are parasitic in warm-blooded animals, such as *Lucilia sericata* or *Lucilia cuprina* (sensitive and resistant strains), *Chrysomya chloropyga* and larvae of warble flies, for example the ox warble fly *Hypoderma bovis*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxides, (etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides or rodenticides, fungicides, bactericides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and nematodes, and more particularly methods of combating at least one of insects and acarids, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

$LT_{100}$ test for Diptera

Test insects: *Musca domestica* (resistant to phosphoric acid esters)

Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test was continuously observed. The time which was necessary for 100% destruction was determined.

The test, the active compounds, the concentrations of the active compounds and the times at which there was 100% destruction can be seen from the following Table 1:

Table 1

LT$_{100}$ test for Diptera

| Active compounds | | Test animals | Active compound concentration in the solution, in % | LT$_{100}$ |
|---|---|---|---|---|
| 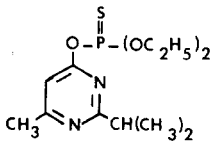 | (known) (C) | Musca domestica Weymann strain | 0.2 0.04 | 210' 6 hrs.=5% |
| | | Musca domestica Sweden I strain | 0.2 0.04 | 6 hrs. 6 hrs.=85% |
| 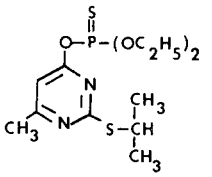 | (known) (A) | Musca domestica Weymann strain | 0.2 | 6 hrs.=0% |
| | | Musca domestica Sweden I strain | 0.2 | 6 hrs.=35% |
| 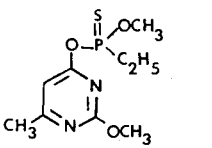 | (5) | Musca domestica Weymann strain | 0.2 0.04 | 120' 4 hrs. |
| | | Musca domstica Sweden I strain | 0.2 0.04 0.008 | 60' 90' 6 hrs. |
| 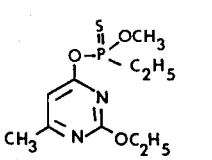 | (44) | Musca domestica Weymann strain | 0.2 0.04 | 150' 4 hrs. |
| | | Musca domestica Sweden I strain | 0.2 0.04 0.008 | 75' 105' 6 hrs.=95% |
| 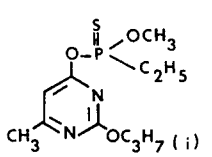 | (53) | Musca domestica Weyman strain | 0.2 0.04 | 150' 6 hrs. |
| | | Musca domestica Sweden I strain | 0.2 0.04 0.008 | 90' 180' 6 hrs.=90% |
| 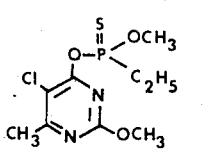 | (29) | Musca domestica Weyman strain | 0.2 0.04 | 180' 6 hrs. |
| | | Musca domestica Sweden I strain | 0.2 0.04 | 90' 150' |

EXAMPLE 2

LD$_{100}$ test
Test insects: Periplaneta americana

Solvent: Acetone
2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test was observed 3 days after the commencement of the experiments. The destruction, in %, was determined.

The active compounds, the concentrations of the active compounds and the results can be seen from the following Table 2:

Table 2

| Active compound | LD$_{100}$ test | |
| --- | --- | --- |
| | Active compound concentration in the solution, in % | Destruction in % |
| 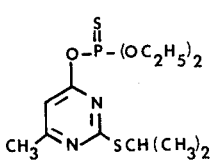 (A) (known) | 0.2 | 60 |
| 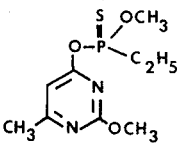 (5) | 0.2<br>0.02 | 100<br>100 |
| 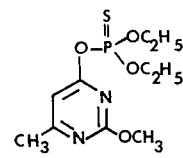 (4) | 0.2<br>0.02<br>0.002 | 100<br>100<br>30 |
| 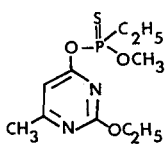 (44) | 0.2<br>0.02 | 100<br>100 |
| 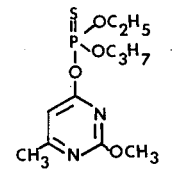 (9) | 0.2<br>0.02 | 100<br>100 |

Table 2-continued

| Active compound | LD$_{100}$ test | |
| --- | --- | --- |
| | Active compound concentration in the solution, in % | Destruction in % |
| (10) | 0.2<br>0.02 | 100<br>100 |
| (13) | 0.2<br>0.02 | 100<br>100 |
| (47) | 0.2<br>0.02 | 100<br>100 |
| (56) | 0.2<br>0.02 | 100<br>100 |
| (58) | 0.2<br>0.02 | 100<br>100 |
| (11) | 0.2<br>0.02 | 100<br>100 |

Table 2-continued

| Active compound | | Active compound concentration in the solution, in % | Destruction in % |
|---|---|---|---|
| 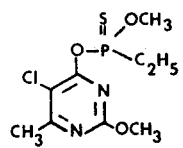 | (29) | 0.2 | 100 |
| 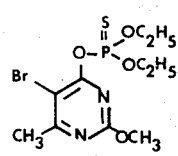 | (27) | 0.2<br>0.02 | 100<br>100 |
| 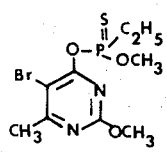 | (24) | 0.2 | 100 |
| 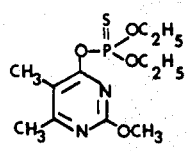 | (22) | 0.2<br>0.02 | 100<br>60 |
| 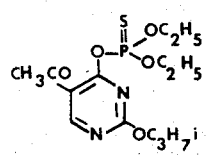 | (75) | 0.2 | 100 |
| 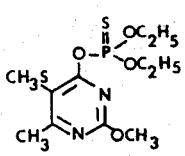 | (33) | 0.2 | 100 |
| 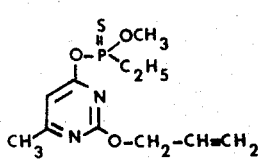 | (100) | 0.2<br>0.02 | 100<br>100 |

Table 2-continued

| Active compound | | Active compound concentration in the solution, in % | Destruction in % |
|---|---|---|---|
| | (96) | 0.2 | 100 |
| | (12) | 0.2 | 100 |

EXAMPLE 3

$LD_{100}$ test

Test insects: *Sitophilus granarius*

Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. Around 25 test insects were then placed in the Petri dish and it was covered with a glass lid.

The condition of the test was observed 3 days after the commencement of the experiments. The destruction, in %, was determined.

The active compounds, the concentrations of the active compounds and the results can be seen from the following Table 3:

Table 3

| Active compound | Active compound concentration in the solution, in % | Destruction in % |
|---|---|---|
| (known) (A) | 0.2<br>0.02<br>0.002 | 100<br>100<br>0 |

Table 3-continued

| Active compound | LD₁₀₀ test | Active compound concentration in the solution, in % | Destruction in % |
|---|---|---|---|
| 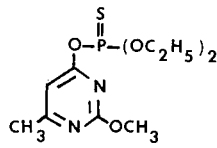 | (4) | 0.2<br>0.02<br>0.002 | 100<br>100<br>100 |
| 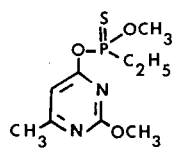 | (5) | 0.2<br>0.02<br>0.002 | 100<br>100<br>100 |
| 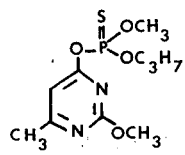 | (10) | 0.2<br>0.02<br>0.002 | 100<br>100<br>100 |
| 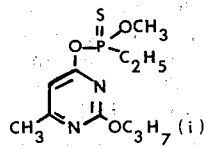 | (53) | 0.2<br>0.02<br>0.002 | 100<br>100<br>100 |

Table 3-continued

| Active compound | LD₁₀₀ test | Active compound concentration in the solution, in % | Destruction in % |
|---|---|---|---|
| 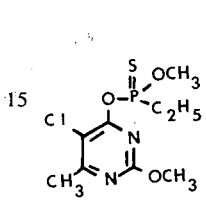 | (29) | 0.2<br>0.02<br>0.002 | 100<br>100<br>100 |

EXAMPLE 4

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed.

The active compounds, the concentrations of the active compounds, the evaluation times and the degree of destruction can be seen from the following Table 4:

Table 4
(*Drosophila* test)

| Active compound | | Active compound concentration in % | Degree of destruction in % after 1 day |
|---|---|---|---|
| 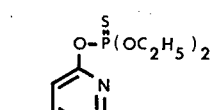<br>(known from Swiss Pat. 321,868) | (D) | 0.1<br>0.01<br>0.001<br>0.0001 | 100<br>100<br>50<br>0 |
| 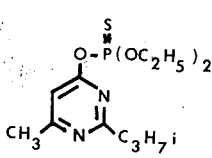<br>(known) | (C) | 0.1<br>0.01<br>0.001<br>0.0001 | 100<br>100<br>60<br>0 |

Table 4-continued
(*Drosophila* test)
| Active compound | | Active compound concentration in % | Degree of destruction in % after 1 day |
|---|---|---|---|
| 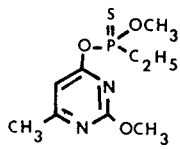 | (5) | 0.1<br>0.01<br>0.001<br>0.0001 | 100<br>100<br>100<br>100 |
| 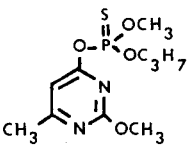 | (10) | 0.1<br>0.01<br>0.001<br>0.0001 | 100<br>100<br>100<br>50 |
| 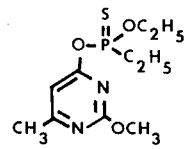 | (13) | 0.1<br>0.01<br>0.001<br>0.0001 | 100<br>100<br>100<br>98 |
| 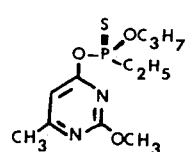 | (11) | 0.1<br>0.01<br>0.001<br>0.0001 | 100<br>100<br>100<br>70 |
| 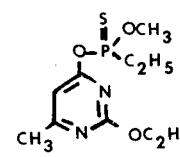 | (44) | 0.1<br>0.01<br>0.001<br>0.0001 | 100<br>100<br>100<br>100 |
| 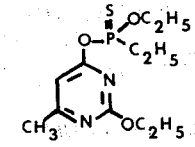 | (47) | 0.1<br>0.01<br>0.001<br>0.0001 | 100<br>100<br>100<br>100 |
| 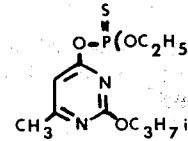 | (52) | 0.1<br>0.01<br>0.001<br>0.0001 | 100<br>100<br>100<br>70 |

Table 4-continued (*Drosophila* test)

| Active compound | | Active compound concentration in % | Degree of destruction in % after 1 day |
|---|---|---|---|
| 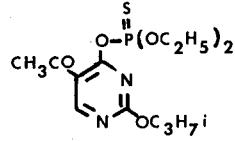 | (75) | 0.1<br>0.01<br>0.001<br>0.0001 | 100<br>100<br>100<br>100 |
| 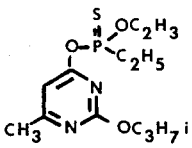 | (56) | 0.1<br>0.01<br>0.001<br>0.0001 | 100<br>100<br>100<br>100 |
| 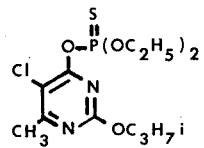 | (79) | 0.1<br>0.01<br>0.001<br>0.0001 | 100<br>100<br>100<br>70 |
| 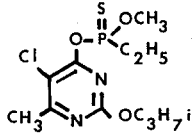 | (80) | 0.1<br>0.01<br>0.001<br>0.0001 | 100<br>100<br>100<br>100 |

EXAMPLE 5

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 5:

Table 5
(*Plutella* test)
| Active compound | | Active compound concentration in % | Degree of destruction in % after 3 days |
|---|---|---|---|
| 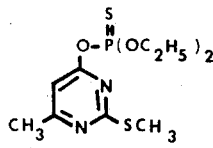 (known) | (A) | 0.1<br>0.01 | 100<br>0 |
| 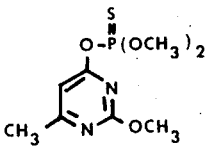 | (6) | 0.1<br>0.01 | 100<br>100 |
| 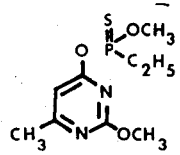 | (5) | 0.1<br>0.01 | 100<br>100 |
| 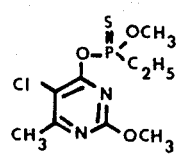 | (29) | 0.1<br>0.01 | 100<br>100 |
| 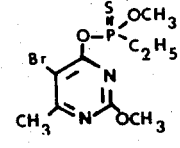 | (24) | 0.1<br>0.01 | 100<br>90 |
| 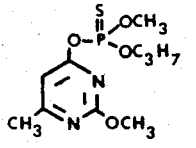 | (10) | 0.1<br>0.01<br>0.001 | 100<br>100<br>45 |
| 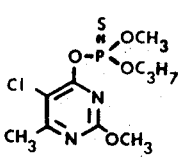 | (28) | 0.1<br>0.01 | 100<br>100 |

Table 5-continued
(*Plutella* test)

| Active compound | | Active compound concentration in % | Degree of destruction in % after 3 days |
|---|---|---|---|
| [structure: 5-Br, 6-CH₃, 2-OCH₃ pyrimidinyl O-P(=S)(OCH₃)(OC₃H₇)] | (23) | 0.1<br>0.01 | 100<br>100 |
| [structure: 6-CH₃, 2-OCH₃ pyrimidinyl O-P(=S)(OC₂H₅)₂] | (4) | 0.1<br>0.01<br>0.001 | 100<br>100<br>95 |
| [structure: 6-CH₃, 2-OCH₃ pyrimidinyl O-P(=O)(OC₂H₅)₂] | (12) | 0.1<br>0.01<br>0.001 | 100<br>100<br>35 |
| [structure: 5-CH₃, 6-CH₃, 2-OCH₃ pyrimidinyl O-P(=S)(OC₂H₅)₂] | (22) | 0.1<br>0.01 | 100<br>100 |
| [structure: 5-CH₃S, 6-CH₃, 2-OCH₃ pyrimidinyl O-P(=S)(OC₂H₅)₂] | (33) | 0.1<br>0.01 | 100<br>100 |
| [structure: 5-Cl, 6-CH₃, 2-OCH₃ pyrimidinyl O-P(=S)(OC₂H₅)₂] | (2) | 0.1<br>0.01 | 100<br>100 |
| [structure: 5-Br, 6-CH₃, 2-OCH₃ pyrimidinyl O-P(=S)(OC₂H₅)₂] | (27) | 0.1<br>0.01 | 100<br>100 |

Table 5-continued

| Active compound | (*Plutella* test) | Active compound concentration in % | Degree of destruction in % after 3 days |
|---|---|---|---|
| [structure with O-P(S)(OC₂H₅)₂, CH₃O-CO-CH₂, OCH₃ on pyrimidine] | (19) | 0.1<br>0.01 | 100<br>100 |
| [structure with O-P(O)(OC₂H₅)₂, CH₃O-CO-CH₂, OCH₃ on pyrimidine] | (18) | 0.1<br>0.01 | 100<br>100 |
| [structure with O-P(S)(OC₂H₅)(C₆H₅), CH₃, OCH₃ on pyrimidine] | (15) | 0.1<br>0.01<br>0.001 | 100<br>100<br>80 |
| [structure with O-P(S)(OC₂H₅)(C₆H₅), Cl, CH₃, OCH₃ on pyrimidine] | (31) | 0.1<br>0.01 | 100<br>100 |
| [structure with O-P(S)(OC₂H₅)(C₆H₅), CH₃O-CO-CH₂, OCH₃ on pyrimidine] | (17) | 0.1<br>0.01 | 100<br>100 |
| [structure with O-P(S)(OC₂H₅)(C₂H₅), CH₃, OCH₃ on pyrimidine] | (13) | 0.1<br>0.01<br>0.001 | 100<br>100<br>100 |
| [structure with O-P(S)(OC₂H₅)(C₂H₅), Br, CH₃, OCH₃ on pyrimidine] | (25) | 0.1<br>0.01 | 100<br>100 |

Table 5-continued
(*Plutella* test)

| Active compound | | Active compound concentration in % | Degree of destruction in % after 3 days |
|---|---|---|---|
| [structure with S=P(OC₂H₅)(SC₃H₇), pyrimidine with CH₃, OCH₃] | (7) | 0.1<br>0.01<br>0.001 | 100<br>100<br>50 |
| [structure with S=P(OC₂H₅)(OC₃H₇), pyrimidine with CH₃, OCH₃] | (9) | 0.1<br>0.01 | 100<br>100 |
| [structure with S=P(OC₃H₇)(C₂H₅), pyrimidine with CH₃, OCH₃] | (11) | 0.1<br>0.01<br>0.001 | 100<br>100<br>100 |
| [structure with S=P(OC₃H₇)(C₂H₅), Cl-pyrimidine with CH₃, OCH₃] | (30) | 0.1<br>0.01 | 100<br>100 |
| [structure with S=P(OC₃H₇)(C₂H₅), pyrimidine with CH₃OCOCH₂, OCH₃] | (16) | 0.1<br>0.01 | 100<br>100 |
| [structure with S=P(OCH₃)₂, pyrimidine with CH₃, OC₂H₅] | (40) | 0.1<br>0.01 | 100<br>100 |
| [structure with S=P(OCH₃)(C₂H₅), pyrimidine with CH₃, OC₂H₅] | (44) | 0.1<br>0.01<br>0.001 | 100<br>100<br>95 |

Table 5-continued

| Active compound | (*Plutella* test) | Active compound concentration in % | Degree of destruction in % after 3 days |
|---|---|---|---|
| [structure with P(S)(OCH₃)(OC₃H₇), pyrimidine with CH₃ and OC₂H₅] (43) | | 0.1<br>0.01<br>0.001 | 100<br>100<br>40 |
| [structure with P(S)(OC₂H₅)₂, pyrimidine with CH₃ and OC₂H₅] (41) | | 0.1<br>0.01<br>0.001 | 100<br>100<br>90 |
| [structure with P(S)(OC₂H₅)(C₆H₅), pyrimidine with CH₃ and OC₂H₅] (46) | | 0.1<br>0.01<br>0.001 | 100<br>100<br>30 |
| [structure with P(S)(OC₂H₅)(C₂H₅), pyrimidine with CH₃ and OC₂H₅] (47) | | 0.1<br>0.01<br>0.001 | 100<br>100<br>100 |
| [structure with P(S)(OC₂H₅)(OC₂H₄-OC₂H₅), pyrimidine with CH₃ and OC₂H₅] (45) | | 0.1<br>0.01 | 100<br>100 |
| [structure with P(S)(OC₂H₅)(OC₃H₇), pyrimidine with CH₃ and OC₂H₅] (42) | | 0.1<br>0.01<br>0.001 | 100<br>100<br>60 |
| [structure with P(S)(OC₃H₇)(C₂H₅), pyrimidine with CH₃ and OC₂H₅] (48) | | 0.1<br>0.01<br>0.001 | 100<br>100<br>100 |

Table 5-continued
(*Plutella* test)

| Active compound | | Active compound concentration in % | Degree of destruction in % after 3 days |
|---|---|---|---|
| [structure with S=P(OC$_2$H$_5$)$_2$, pyrimidine with CH$_3$, O-cyclohexyl-H] | (102) | 0.1<br>0.01 | 100<br>100 |
| [structure with S=P(OCH$_3$)(C$_2$H$_5$), pyrimidine with CH$_3$, O-CH$_2$-C≡CH] | (96) | 0.1<br>0.01 | 100<br>95 |
| [structure with S=P(OCH$_3$)(C$_2$H$_5$), pyrimidine with CH$_3$, O-CH$_2$-CH=CH$_2$] | (100) | 0.1<br>0.01<br>0.001 | 100<br>100<br>100 |
| [structure with S=P(OC$_2$H$_5$)$_2$, pyrimidine with CH$_3$, O-CH$_2$-C≡CH] | (97) | 0.1<br>0.01<br>0.001 | 100<br>100<br>30 |
| [structure with S=P(OC$_2$H$_5$)$_2$, pyrimidine with CH$_3$, O-CH$_2$-CH=CH$_2$] | (98) | 0.1<br>0.01<br>0.001 | 100<br>100<br>95 |
| [structure with S=P(OC$_2$H$_5$)(phenyl), pyrimidine with CH$_3$, O-CH$_2$-CH=CH$_2$] | (101) | 0.1<br>0.01<br>0.001 | 100<br>100<br>50 |
| [structure with S=P(OC$_3$H$_7$)(C$_2$H$_5$), pyrimidine with CH$_3$, O-CH$_2$-CH=CH$_2$] | (99) | 0.1<br>0.01<br>0.001 | 100<br>100<br>100 |

Table 5-continued
(*Plutella* test)
| Active compound | | Active compound concentration in % | Degree of destruction in % after 3 days |
|---|---|---|---|
| 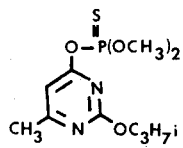 | (50) | 0.1<br>0.01 | 100<br>100 |
| 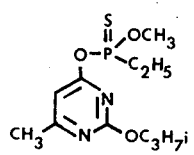 | (53) | 0.1<br>0.01 | 100<br>100 |
| 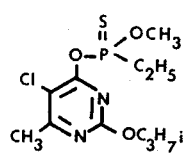 | (80) | 0.1<br>0.01<br>0.001 | 100<br>100<br>95 |
| 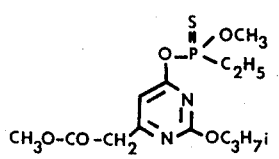 | (68) | 0.1<br>0.01<br>0.01 | 100<br>100<br>100 |
| 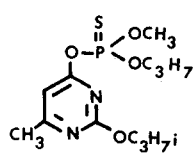 | (49) | 0.1<br>0.01<br>0.001 | 100<br>100<br>100 |
| 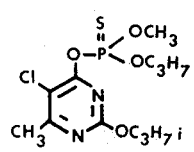 | (82) | 0.1<br>0.01 | 100<br>100 |

Table 5-continued
| Active compound | (Plutella test) | Active compound concentration in % | Degree of destruction in % after 3 days |
|---|---|---|---|
| 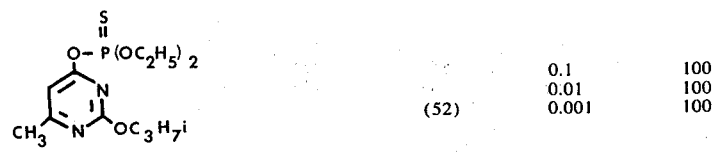 | (52) | 0.1<br>0.01<br>0.001 | 100<br>100<br>100 |
|  | (57) | 0.1<br>0.01 | 100<br>100 |
|  | (78) | 0.1<br>0.01 | 100<br>100 |
|  | (79) | 0.1<br>0.01<br>0.001 | 100<br>100<br>100 |
|  | (84) | 0.1<br>0.01 | 100<br>100 |
|  | (75) | 0.1<br>0.01 | 100<br>100 |
|  | (67) | 0.1<br>0.01 | 100<br>100 |

Table 5-continued

| Active compound | (Plutella test) | Active compound concentration in % | Degree of destruction in % after 3 days |
|---|---|---|---|
| structure with NC, pyrimidine, O-P(S)(OC₂H₅)₂, OC₃H₇i | (70) | 0.1<br>0.01 | 100<br>100 |
| cyclopenta-fused pyrimidine with O-P(S)(OC₂H₅)₂, OC₃H₇i | (94) | 0.1<br>0.01 | 100<br>95 |
| benzo-fused pyrimidine (quinazoline) with O-P(S)(OC₂H₅)₂, OC₃H₇i | (61) | 0.1<br>0.01 | 100<br>100 |
| pyrimidine with CH₃, O-P(S)(OC₂H₅)(C₆H₅), OC₃H₇i | (55) | 0.1<br>0.01<br>0.001 | 100<br>100<br>100 |
| pyrimidine with Cl, CH₃, O-P(S)(OC₂H₅)(C₆H₅), OC₃H₇i | (85) | 0.1<br>0.01<br>0.001 | 100<br>100<br>100 |
| pyrimidine with CH₃O-CO-CH₂, O-P(S)(OC₂H₅)(C₆H₅), OC₃H₇i | (64) | 0.1<br>0.01 | 100<br>100 |
| pyrimidine with CH₃, O-P(S)(OC₂H₅)(C₂H₅), OC₃H₇i | (56) | 0.1<br>0.01<br>0.001 | 100<br>100<br>100 |

Table 5-continued
(*Plutella* test)
| Active compound | | Active compound concentration in % | Degree of destruction in % after 3 days |
|---|---|---|---|
| 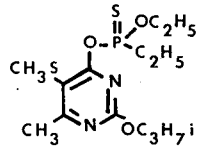 | (87) | 0.1<br>0.01 | 100<br>100 |
| 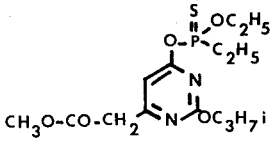 | (65) | 0.1<br>0.01 | 100<br>100 |
| 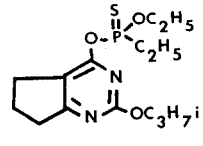 | (95) | 0.1<br>0.01 | 100<br>100 |
| 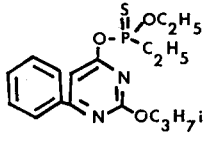 | (62) | 0.1<br>0.01<br>0.001 | 100<br>100<br>40 |
| 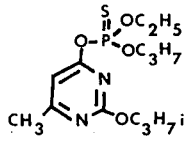 | (51) | 0.1<br>0.01<br>0.001 | 100<br>100<br>100 |
| 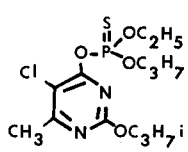 | (83) | 0.1<br>0.01<br>0.001 | 100<br>100<br>65 |
| 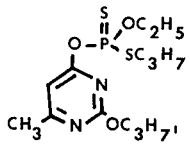 | (59) | 0.1<br>0.01<br>0.001 | 100<br>100<br>80 |

Table 5-continued

| Active compound | (Plutella test) | Active compound concentration in % | Degree of destruction in % after 3 days |
|---|---|---|---|
| [structure with CH3S, CH3, OC2H5, SC3H7, OC3Hi] | (90) | 0.1<br>0.01 | 100<br>100 |
| [structure with Cl, CH3, OC2H5, SC3H7, OC3Hi] | (86) | 0.1<br>0.01 | 100<br>100 |
| [structure with CH3, OC3H7, C2H5, OC3Hi] | (58) | 0.1<br>0.01<br>0.001 | 100<br>100<br>100 |
| [structure with Cl, CH3, OC3H7, C2H5, OC3Hi] | (81) | 0.1<br>0.01<br>0.001 | 100<br>100<br>90 |
| [structure with CH3O-CO-CH2, OC3H7, C2H5, OC3Hi] | (66) | 0.1<br>0.01<br>0.001 | 100<br>100<br>95 |
| [structure with CH3CO, OC3H7, C2H5, OC3Hi] | (77) | 0.1<br>0.01 | 100<br>100 |

EXAMPLE 6

Laphygma test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium barbadense*) were sprayed with the preparation of the active compound until dew moist and were then infested with caterpillars of the owlet moth (*Laphygma exigua*).

After the specified periods of time, the degree of destruction in % was determined. 100% means that all caterpillars had been killed, whereas 0% indicates that no caterpillars had been killed.

The active compounds, the concentrations of the active compounds, the evaluation times and the results can be seen from Table 6 which follows:

Table 6
(*Laphygma* test)

| Active compound | | Active compound concentration in % | Degree of destruction in % after 3 days |
|---|---|---|---|
| 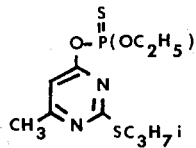 (known) | (A) | 0.1<br>0.01<br>0.001 | 100<br>100<br>0 |
| 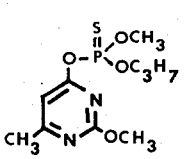 | (10) | 0.1<br>0.01<br>0.001 | 100<br>100<br>95 |
| 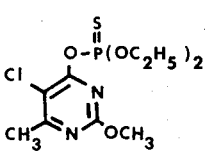 | (2) | 0.1<br>0.01<br>0.001 | 100<br>100<br>95 |
| 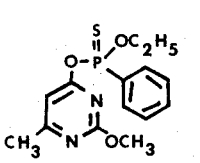 | (15) | 0.1<br>0.01<br>0.001 | 100<br>100<br>100 |
| 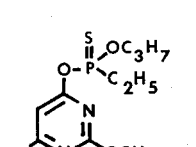 | (11) | 0.1<br>0.01<br>0.001 | 100<br>100<br>100 |
| 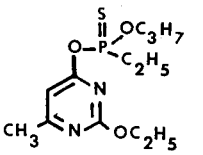 | (48) | 0.1<br>0.01<br>0.001 | 100<br>100<br>100 |

Table 6-continued (*Laphygma* test)

| Active compound | | Active compound concentration in % | Degree of destruction in % after 3 days |
|---|---|---|---|
| structure with $O-P(OC_2H_5)_2$, $S$, pyrimidine with $CH_3$ and $O-CH_2-CH=CH_2$ | (98) | 0.1<br>0.01<br>0.001 | 100<br>100<br>100 |
| structure with $O-P(S)(OC_3H_7)(C_2H_5)$, pyrimidine with $CH_3$ and $O-CH_2-CH=CH_2$ | (99) | 0.1<br>0.01<br>0.001 | 100<br>100<br>100 |
| structure with $O-P(S)(OC_2H_5)(C_6H_5)$, pyrimidine with $CH_3$ and $OC_3H_7i$ | (55) | 0.1<br>0.01<br>0.001 | 100<br>100<br>95 |
| structure with $O-P(S)(OC_3H_7)(C_2H_5)$, pyrimidine with $CH_3$ and $OC_3H_7i$ | (58) | 0.1<br>0.01<br>0.001 | 100<br>100<br>100 |

EXAMPLE 7

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the state amount of emulsifier and the concentrate was diluted with water to the desired concentration.

Bean plants (*Phaseolus vulgaris*), which had a height of approximately 10 – 30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed, whereas 0% means that none of the spider mites were killed.

The active compounds, the concentrations of the active compounds, the evaluation times and the results can be seen from the following Table 7:

Table 7

Tetranychus test (Mites which damage plants)

| Active compound | | Active compound concentration in % | Degree of destruction in % after 2 days |
|---|---|---|---|
| Structure: 4-(diethoxyphosphinothioyloxy)-6-methyl-2-methylthio-pyrimidine (known) | (B) | 0.1 | 0 |
| Structure: 4-(diethoxyphosphinothioyloxy)-6-methyl-2-isopropylthio-pyrimidine (known) | (A) | 0.1 | 0 |
| Structure: methyl ethyl phosphonothioate ester of 2-methoxy-6-methyl-4-hydroxypyrimidine | (5) | 0.1 | 99 |
| Structure: methyl propyl phosphorothioate of 2-methoxy-6-methyl-4-hydroxypyrimidine | (10) | 0.1<br>0.01 | 98<br>80 |
| Structure: diethyl phosphorothioate of 2-methoxy-6-methyl-4-hydroxypyrimidine | (4) | 0.1<br>0.01 | 98<br>95 |
| Structure: diethyl phosphate of 2-methoxy-6-methyl-4-hydroxypyrimidine | (12) | 0.1 | 95 |
| Structure: diethyl phosphate of 5-methylthio-2-methoxy-6-methyl-4-hydroxypyrimidine | (38) | 0.1 | 90 |

Table 7-continued

Tetranychus test (Mites which damage plants)

| Active compound | | Active compound concentration in % | Degree of destruction in % after 2 days |
|---|---|---|---|
| [Structure: 5-Br, 6-CH$_3$, 2-OCH$_3$ pyrimidin-4-yl O-P(=S)(OC$_2$H$_5$)$_2$] | (27) | 0.1 | 98 |
| [Structure: 6-(CH$_3$O-CO-CH$_2$), 2-OCH$_3$ pyrimidin-4-yl O-P(=S)(OC$_2$H$_5$)$_2$] | (19) | 0.1 | 100 |
| [Structure: 6-CH$_3$, 2-OCH$_3$ pyrimidin-4-yl O-P(=S)(OC$_2$H$_5$)(C$_2$H$_5$)] | (13) | 0.1 | 98 |
| [Structure: 6-CH$_3$, 2-OCH$_3$ pyrimidin-4-yl O-P(=S)(OC$_2$H$_5$)(NH-C$_3$H$_7$i)] | (14) | 0.1 | 95 |
| [Structure: 5-SCH$_3$, 6-CH$_3$, 2-OCH$_3$ pyrimidin-4-yl O-P(=S)(OC$_2$H$_5$)(SC$_3$H$_7$)] | (36) | 0.1 | 100 |
| [Structure: 6-CH$_3$, 2-OCH$_3$ pyrimidin-4-yl O-P(=S)(OC$_3$H$_7$)(C$_2$H$_5$)] | (11) | 0.1 | 100 |
| [Structure: 6-CH$_3$, 2-OC$_2$H$_5$ pyrimidin-4-yl O-P(=S)(OCH$_3$)$_2$] | (40) | 0.1 | 100 |

Table 7-continued
Tetranychus test (Mites which damage plants)
| Active compound | | Active compound concentration in % | Degree of destruction in % after 2 days |
|---|---|---|---|
| 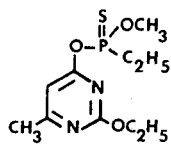 | (44) | 0.1<br>0.01 | 100<br>50 |
| 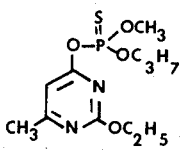 | (43) | 0.1<br>0.01 | 100<br>80 |
| 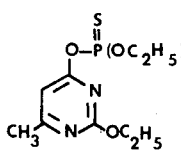 | (41) | 0.1 | 98 |
| 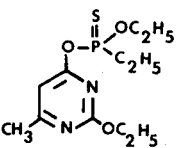 | (47) | 0.1 | 98 |
| 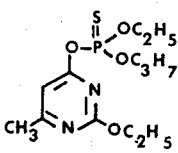 | (42) | 0.1 | 98 |
| 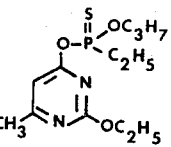 | (48) | 0.1 | 100 |
| 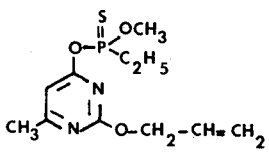 | (100) | 0.1 | 98 |

Table 7-continued

*Tetranychus* test (Mites which damage plants)

| Active compound | | Active compound concentration in % | Degree of destruction in % after 2 days |
|---|---|---|---|
| [structure with O-P(S)(OC₂H₅)₂, pyrimidine ring, CH₃, O-CH₂-C≡CH] | (97) | 0.1 | 90 |
| [structure with O-P(S)(OC₃H₇)(C₂H₅), pyrimidine ring, CH₃, O-CH₂-CH=CH₂] | (99) | 0.1 | 98 |
| [structure with O-P(S)(OCH₃)₂, pyrimidine ring, CH₃, OC₃H₇i] | (50) | 0.1 | 98 |
| [structure with O-P(S)(OCH₃)(C₂H₅), pyrimidine ring, CH₃, OC₃H₇i] | (53) | 0.1<br>0.01 | 100<br>60 |
| [structure with O-P(S)(OCH₃)(C₂H₅), pyrimidine ring with Cl, CH₃, OC₃H₇i] | (80) | 0.1 | 90 |
| [structure with O-P(S)(OCH₃)(C₂H₅), pyrimidine ring, CH₃O-CO-CH₂, OC₃H₇i] | (68) | 0.1 | 98 |
| [structure with O-P(S)(OCH₃)(OC₃H₇), pyrimidine ring, CH₃, OC₃H₇i] | (49) | 0.1<br>0.01 | 98<br>30 |

Table 7-continued
Tetranychus test (Mites which damage plants)
| Active compound | | Active compound concentration in % | Degree of destruction in % after 2 days |
|---|---|---|---|
| 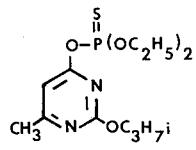 | (52) | 0.1<br>0.01 | 98<br>60 |
| 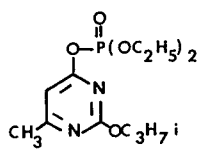 | (57) | 0.1 | 90 |
| 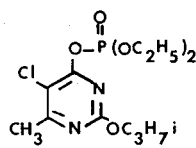 | (84) | 0.1 | 100 |
| 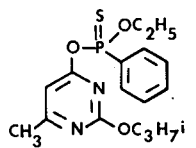 | (55) | 0.1 | 95 |
| 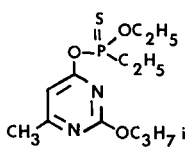 | (56) | 0.1 | 98 |
| 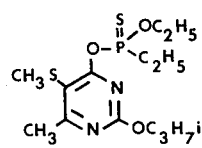 | (87) | 0.1 | 90 |
| 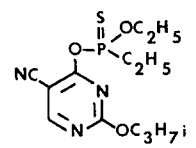 | (3) | 0.1 | 100 |

Table 7-continued

Tetranychus test (Mites which damage plants)

| Active compound | | Active compound concentration in % | Degree of destruction in % after 2 days |
|---|---|---|---|
| [structure] | (65) | 0.1 | 100 |
| [structure] | (95) | 0.1 | 98 |
| [structure] | (59) | 0.1<br>0.01 | 100<br>35 |
| [structure] | (86) | 0.1 | 100 |
| [structure] | (54) | 0.1 | 90 |
| [structure] | (58) | 0.1 | 100 |
| [structure] | (81) | 0.1 | 100 |

Table 7-continued

| Active compound | Tetranychus test (Mites which damage plants) | Active compound concentration in % | Degree of destruction in % after 2 days |
|---|---|---|---|
| 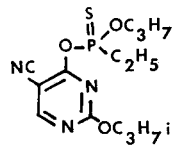 (72) | | 0.1 | 95 |

EXAMPLE 8

Test with parasitic fly larvae
Solvent: 35 parts by weight of ethylene polyglycol monomethyl ether
Emulsifier: 35 parts by weight of nonylphenol polyglycol ether To produce a suitable preparation of active compound, 30 parts by weight of the active substance in question were mixed with the stated amount of solvent which contained the above-mentioned proportion of nonylphenol polyglycol ether and the concentrate thus obtained was diluted with water to the desired concentration.

About 20 fly larvae (*Lucilia cuprina* cuprina) were introduced into a test tube which contained approximately 2 ml of horse muscle. 0.5 ml of the preparation of active compound was applied to this horse meat. After 24 hours, the degree of destruction in % was determined. 100% means that all larvae had been killed and 0 % means that no larvae had been killed.

The active compounds tested, active-compound concentrations used and results obtained can be seen from Table 8 which follows:

Table 8

(Test with parasitic fly larvae/*Lucilia cuprina* res.)

| Active compound | | Active compound concentration in ppm | Degree of destruction in % |
|---|---|---|---|
| 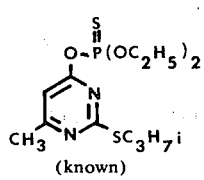 (known) | (A) | 100<br>30<br>10<br>3 | 100<br>100<br>100<br>0 |
| 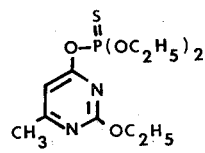 | (41) | 100<br>30<br>10<br>3<br>1 | 100<br>100<br>100<br>100<br>0 |
| 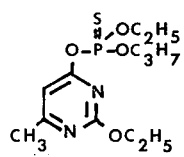 | (42) | 100<br>30<br>10<br>3<br>1 | 100<br>100<br>100<br>100<br>0 |

Table 8-continued (Test with parasitic fly larvae/*Lucilia cuprina* res.)

| Active compound | | Active compound concentration in ppm | Degree of destruction in % |
|---|---|---|---|
| [structure: S=P(C2H5)(OCH3)-O-pyrimidine with CH3 and OC3H7i] | (53) | 100<br>30<br>10<br>3<br>1<br>0.3 | 100<br>100<br>100<br>100<br>100<br>0 |
| [structure: S=P(OC2H5)(NHC3H7i)-O-pyrimidine with CH3 and OCH3] | (14) | 100<br>30<br>10<br>3<br>1<br>0.3<br>0.1 | 100<br>100<br>100<br>100<br>100<br>>50<br>0 |
| [structure: S=P(OC2H5)(phenyl)-O-pyrimidine with CH3 and OCH(CH3)2] | (55) | 100<br>30<br>10<br>3<br>1<br>0.3 | 100<br>100<br>100<br>100<br>100<br>0 |
| [structure: S=P(C2H5)(OC2H5)-O-pyrimidine with CH3 and OCH3] | (13) | 100<br>30<br>10<br>3<br>1<br>0.3 | 100<br>100<br>100<br>100<br>100<br>0 |
| [structure: S=P(C2H5)(OCH3)-O-pyrimidine with Br, CH3 and OCH3] | (24) | 100<br>30<br>10<br>3<br>1 | 100<br>100<br>100<br>100<br>0 |
| [structure: S=P(C2H5)(OCH3)-O-pyrimidine with Cl, CH3 and OC3H7i] | (80) | 100<br>30<br>10<br>3<br>1<br>0.3 | 100<br>100<br>100<br>100<br>100<br>0 |
| [structure: S=P(OCH3)(C2H5)-O-pyrimidine with CH3 and OCH3] | (5) | 100<br>10<br>1<br>0.1 | 100<br>100<br>100<br>0 |

Table 8-continued (Test with parasitic fly larvae/*Lucilia cuprina* res.)

| Active compound | | Active compound concentration in ppm | Degree of destruction in % |
|---|---|---|---|
| [structure] | (49) | 100<br>30<br>10<br>3<br>1 | 100<br>100<br>100<br>>50<br>0 |
| [structure] | (79) | 100<br>30<br>10<br>3<br>1<br>0.3<br>0.1 | 100<br>100<br>100<br>100<br>>50<br>>50<br>0 |
| [structure] | (16) | 100<br>30<br>10<br>3<br>1<br>0.3 | 100<br>100<br>100<br>100<br>>50<br>0 |
| [structure] | (17) | 100<br>30<br>10<br>3<br>1 | 100<br>100<br>100<br>100<br>0 |
| [structure] | (18) | 100<br>30<br>10<br>3<br>1<br>0.3<br>0.1 | 100<br>100<br>100<br>100<br>100<br>100<br>0 |
| [structure] | (83) | 100<br>30<br>10<br>3<br>1<br>0.3 | 100<br>100<br>100<br>>50<br><50<br>0 |

Table 8-continued (Test with parasitic fly larvae/*Lucilia cuprina* res.)

| Active compound | | Active compound concentration in ppm | Degree of destruction in % |
|---|---|---|---|
| [structure with Cl, CH$_3$, OCH$_3$, C$_2$H$_5$, OCH$_3$] | (29) | 100<br>30<br>10<br>3<br>1<br>0.3 | 100<br>100<br>100<br>100<br>100<br>0 |
| [structure with Cl, CH$_3$, OC$_2$H$_5$, phenyl, OCH$_3$] | (31) | 100<br>30<br>10<br>3<br>1<br>0.3 | 100<br>100<br>100<br>100<br><50<br>0 |
| [structure with (OC$_2$H$_5$)$_2$, CH$_3$, OC$_3$H$_7$i] | (52) | 100<br>30<br>10<br>3<br>1<br>0.3 | 100<br>100<br>100<br>100<br><50<br>0 |
| [structure with OCH$_3$, C$_2$H$_5$, CH$_3$, O-CH$_2$-CH=CH$_2$] | (100) | 100<br>30<br>10<br>3<br>1 | 100<br>100<br>100<br>100<br>0 |

EXAMPLE 9

Critical concentration test/soil insects
Test insect: *Phorbia brassicae* grubs
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which was quoted in ppm (for example mg/l). The soil was filled into pots and the pots were left to stand at room temperature After 24 hours the test insects were introduced into the treated soil and after a further 48 hours the degree of effectiveness of the active compound was determined in % by counting the dead and live test insects. The degree of effectiveness was 100% if all test insects had been killed and was 0% if exactly as many test insects were still alive as in the case of the control.

The active compounds, amounts used and results can be seen from the Table 9 which follows:

Table 9
(*Phorbia brassicae* grubs in the soil)
| Active compound | Degree of destruction in % at an active compound concentration of | | | | | |
|---|---|---|---|---|---|---|
| | 20 | 10 | 5 | 2.5 | 1.25 | 0.625 ppm |
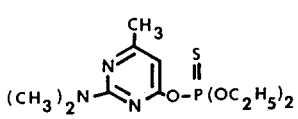
(known from South African Patent Specification 64/1333)
(E)
| | 95 | 50 | 0 | | | |
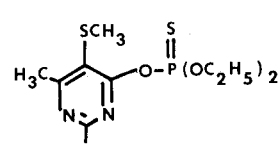
(33)
| | 100 | 100 | 100 | 100 | 50 | |
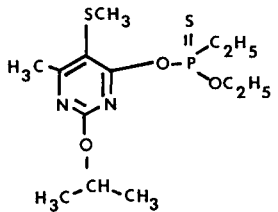
(87)
| | 100 | 100 | 90 | 50 | | |
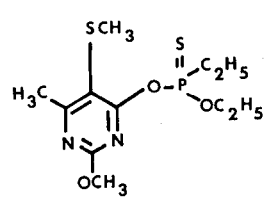
(34)
| | 100 | 100 | 99 | 50 | | |
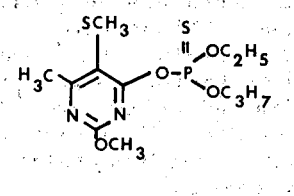
(35)
| | 100 | 100 | 95 | 50 | | |
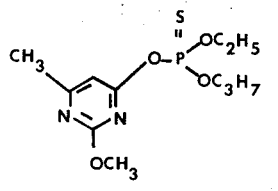
(9)
| | 100 | 100 | 100 | 100 | 100 | 80 |

Table 9-continued

| Active compound | (*Phorbia brassicae* grubs in the soil) Degree of destruction in % at an active compound concentration of | | | | | |
|---|---|---|---|---|---|---|
| | 20 | 10 | 5 | 2.5 | 1.25 | 0.625 ppm |
| (7) | 100 | 100 | 90 | 50 | | |
| (41) | 100 | 100 | 100 | 100 | 100 | 90 |
| (42) | 100 | 100 | 100 | 100 | 100 | 100 |
| | 100 | 100 | 100 | 100 | 100 | 100 |
| (52) | 100 | 100 | 100 | 100 | 98 | 50 |

Table 9-continued
| Active compound | (*Phorbia brassicae* grubs in the soil) Degree of destruction in % at an active compound concentration of | | | | | |
|---|---|---|---|---|---|---|
| | 20 | 10 | 5 | 2.5 | 1.25 | 0.625 ppm |
| 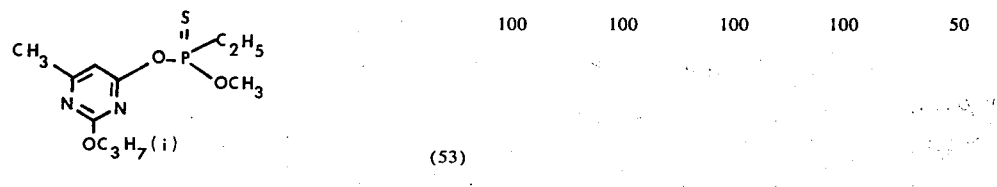 (53) | 100 | 100 | 100 | 100 | 50 | |
| 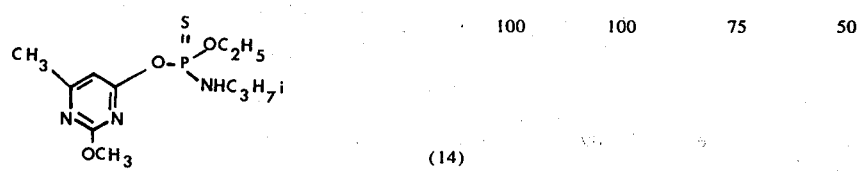 (14) | 100 | 100 | 75 | 50 | | |
| 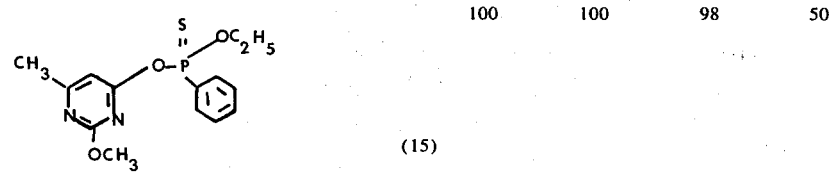 (15) | 100 | 100 | 98 | 50 | | |
| 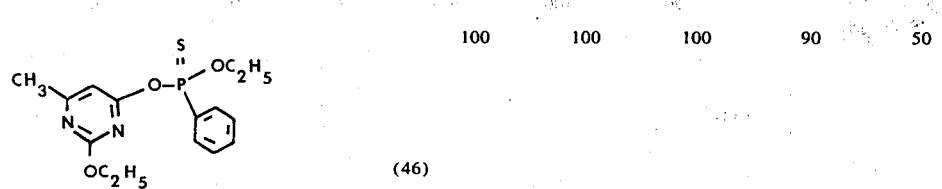 (46) | 100 | 100 | 100 | 90 | 50 | |
| 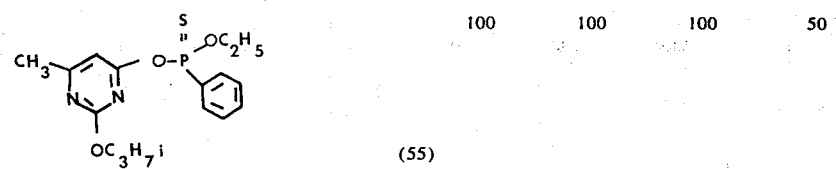 (55) | 100 | 100 | 100 | 50 | | |
| 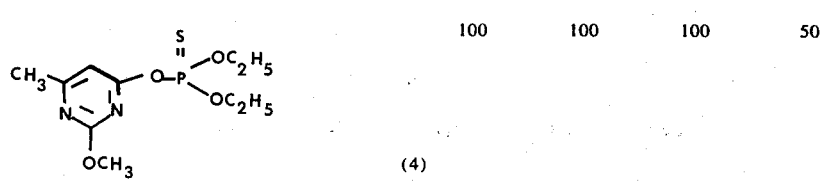 (4) | 100 | 100 | 100 | 50 | | |

Table 9-continued
(*Phorbia brassicae* grubs in the soil)
| Active compound | Degree of destruction in % at an active compound concentration of | | | | | |
|---|---|---|---|---|---|---|
| | 20 | 10 | 5 | 2.5 | 1.25 | 0.625 ppm |
| 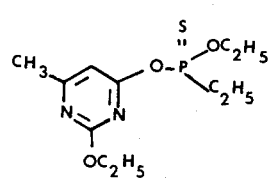 (47) | 100 | 100 | 100 | 50 | | |
| 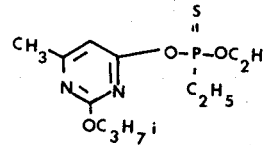 (56) | 100 | 100 | 100 | 100 | 100 | 75 |
| 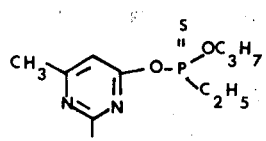 (58) | 100 | 100 | 100 | 100 | 50 | |
| 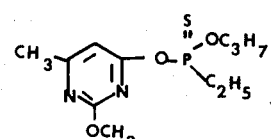 (11) | 100 | 100 | 100 | 100 | 50 | |
| 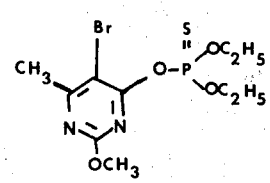 (27) | 100 | 100 | 100 | 100 | 50 | |
| 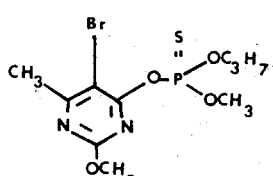 (23) | 100 | 100 | 99 | 50 | | |

Table 9-continued
(*Phorbia brassicae* grubs in the soil)
| Active compound | Degree of destruction in % at an active compound concentration of | | | | | |
|---|---|---|---|---|---|---|
| | 20 | 10 | 5 | 2.5 | 1.25 | 0.625 ppm |
| 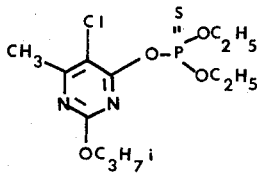 (79) | 100 | 100 | 100 | 100 | 95 | 50 |
| 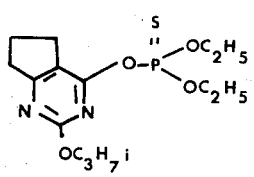 (94) | 100 | 100 | 100 | 100 | 50 | |
| 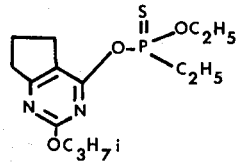 (95) | 100 | 100 | 100 | 95 | 50 | |
| 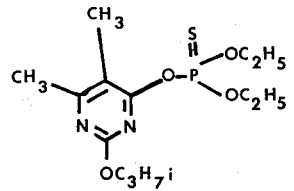 (78) | 100 | 100 | 100 | 50 | | |
| 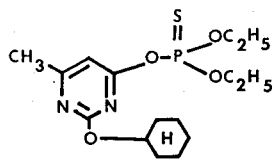 (102) | 100 | 100 | 100 | 50 | | |
| 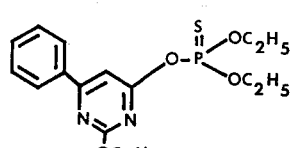 (61) | 100 | 100 | 100 | 75 | | |

Table 9-continued (*Phorbia brassicae* grubs in the soil)

| Active compound | Degree of destruction in % at an active compound concentration of | | | | | |
|---|---|---|---|---|---|---|
| | 20 | 10 | 5 | 2.5 | 1.25 | 0.625 ppm |
| (62) Phenyl-pyrimidinyl phosphonothioate with OC$_2$H$_5$, C$_2$H$_5$, OC$_3$H$_7$i | 100 | 100 | 100 | 75 | | |
| (59) CH$_3$-pyrimidinyl with OC$_2$H$_5$, SC$_3$H$_7$, OC$_3$H$_7$i | 100 | 100 | 100 | 50 | | |
| (22) Dimethyl-pyrimidinyl with OC$_2$H$_5$, OC$_2$H$_5$, OCH$_3$ | 100 | 100 | 100 | 95 | 50 | |
| (81) Cl, CH$_3$-pyrimidinyl with OC$_3$H$_7$, C$_2$H$_5$, OC$_3$H$_7$i | 100 | 100 | 98 | 50 | | |
| (83) Cl, CH$_3$-pyrimidinyl with OC$_3$H$_7$, OC$_2$H$_5$, OC$_3$H$_7$i | 100 | 100 | 100 | 100 | 100 | 100 |
| (30) Cl, CH$_3$-pyrimidinyl with C$_2$H$_5$, OC$_3$H$_7$, OCH$_3$ | 100 | 100 | 90 | 50 | | |

Table 9-continued
| Active compound | (*Phorbia brassicae* grubs in the soil) Degree of destruction in % at an active compound concentration of | | | | | |
|---|---|---|---|---|---|---|
| | 20 | 10 | 5 | 2.5 | 1.25 | 0.625 ppm |
| 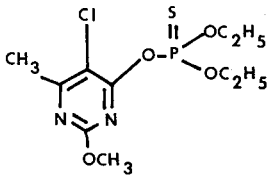 (2) | 100 | 100 | 100 | 100 | 50 | |
| 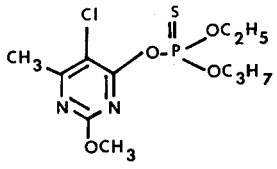 (32) | 100 | 100 | 100 | 100 | 50 | |
| 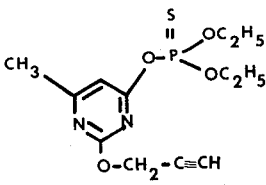 (97) | 100 | 100 | 100 | 100 | 50 | |
| 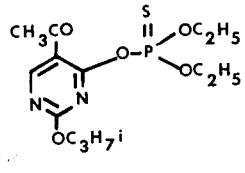 (75) | 100 | 100 | 100 | 95 | 50 | |
| 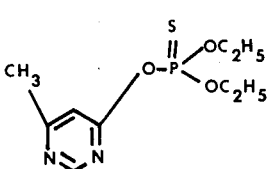 (98) | 100 | 100 | 100 | 100 | 95 | 50 |
| 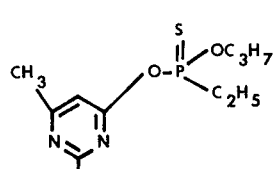 (99) | 100 | 100 | 100 | 95 | 50 | |

EXAMPLE 10

Critical concentration test/soil insects
Test insect: *Tenebrio molitor* larvae
Solvent: 3 Parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which was quoted in ppm (for example mg/1). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness was 100% if all test insects had been killed and was 0% if exactly as many test insects were still alive as in the case of the control.

The active compounds, amounts used and results can be seen from the Table 10 which follows:

Table 10

| Active compound | (*Tenebrio molitor* larvae in the soil) Degree of destruction in % at an active compound concentration of | | | | |
|---|---|---|---|---|---|
| | 20 | 10 | 5 | 2.5 | 1.25 ppm |
| 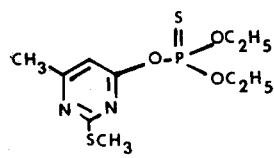 (B) (known) | | 90 | | | |
| 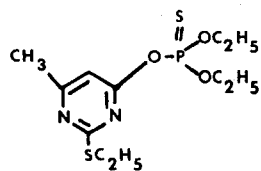 (D) (known) | | 100 | 50 | | |
| 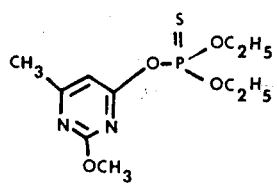 (4) | 100 | 100 | 100 | 50 | |

Table 10-continued
(*Tenebrio molitor* larvae in the soil)
| Active compound | Degree of destruction in % at an active compound concentration of | | | | |
|---|---|---|---|---|---|
| | 20 | 10 | 5 | 2.5 | 1.25 ppm |
| 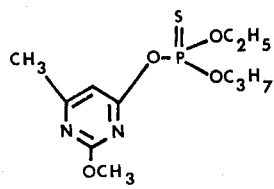 (9) | | 100 | 100 | 100 | 50 |
| 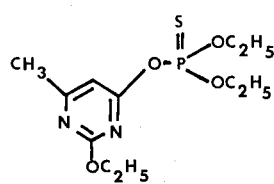 (41) | | 100 | 100 | 75 | 50 |
| 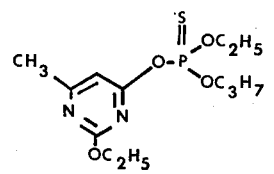 (42) | | 100 | 100 | 100 | 50 |
| 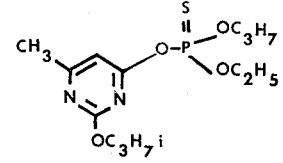 (51) | | 100 | 100 | 90 | 50 |
| 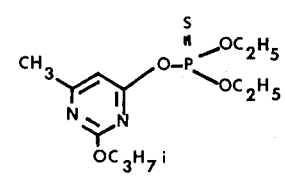 (52) | | 100 | 100 | 75 | 50 |

Table 10-continued
(*Tenebrio molitor* larvae in the soil)
| Active compound | Degree of destruction in % at an active compound concentration of | | | | |
|---|---|---|---|---|---|
| | 20 | 10 | 5 | 2.5 | 1.25 ppm |
| 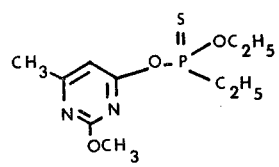 (13) | 100 | 100 | 75 | 50 | |
| 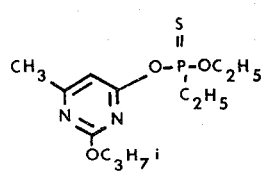 (56) | 100 | 100 | 75 | 50 | |
| 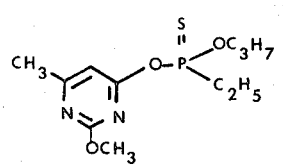 (11) | 100 | 100 | 95 | 50 | |
| 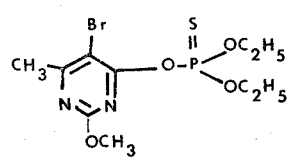 (27) | 100 | 100 | 100 | 100 | 30 |
| 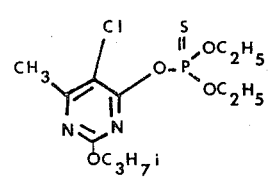 (79) | 100 | 100 | 100 | 50 | |

Table 10-continued
| Active compound | (*Tenebrio molitor* larvae in the soil) Degree of destruction in % at an active compound concentration of | | | | |
|---|---|---|---|---|---|
| | 20 | 10 | 5 | 2.5 | 1.25 ppm |
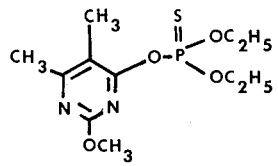
(22)
100  100  100  50
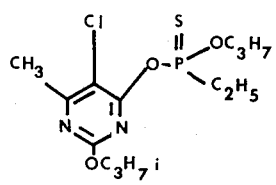
(81)
100  100  90  50
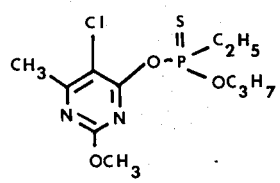
(30)
100  100  90  50
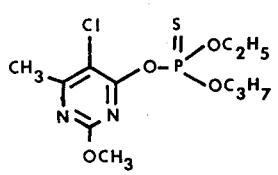
(32)
100  100  90  50
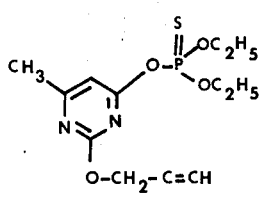
(97)
100  100  100  50
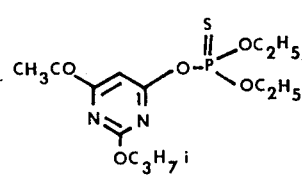
(75)
100  100  100  20

Table 10-continued (*Tenebrio molitor* larvae in the soil)

| Active compound | Degree of destruction in % at an active compound concentration of | | | | |
|---|---|---|---|---|---|
| | 20 | 10 | 5 | 2.5 | 1.25 ppm |
| 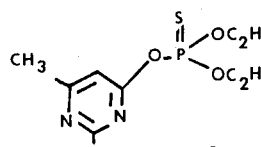 (98) | 100 | 100 | 100 | 50 | |
| 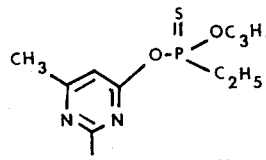 (99) | 100 | 100 | 90 | 50 | |

EXAMPLE 11

Critical concentration test
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in p.p.m., was decisive. The soil was filled into pots, lettuce was sown in and the pots were kept at a greenhouse temperature of 27°C. After 4 weeks, the lettuce roots were examined for infestation with nematodes, and the degree of effectiveness of the active compound was determined as a percentage. The degree of effectiveness was 100% when infestation had been completely avoided; it was 0% when the infestation was exactly the same as in the case of the control plants in untreated soil which had been infested in the same manner.

The active compounds, the amounts applied and the results can be seen from the following Table 11:

Table 11

(*Meloidogyne incognita* test)

| Active compound | Degree of destruction in % at an active compound concentration of | | | | |
|---|---|---|---|---|---|
| | 20 | 10 | 5 | 2.5 | ppm |
| 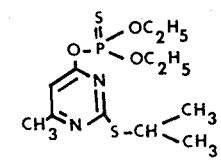 (known) (A) | 98 | 50 | 0 | | |

Table 11-continued
(*Meloidogyne incognita* test)
| Active compound | | Degree of destruction in % at an active compound concentration of | | | |
|---|---|---|---|---|---|
| | | 20 | 10 | 5 | 2.5 ppm |
| 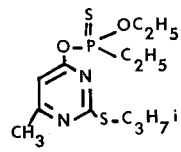 | (F) (known) | | 98 | 50 | 0 |
| 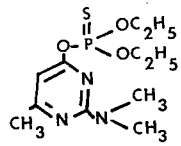 | (known) (E) | 0 | | | |
| 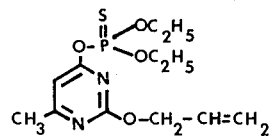 | (98) | 98 | 95 | 50 | |
| 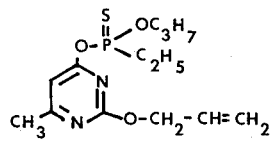 | (99) | 98 | 95 | 50 | |
| 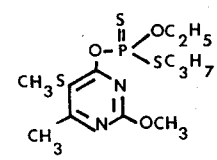 | (36) | 100 | 98 | 95 | 50 |
| 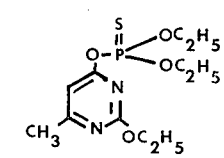 | (41) | 100 | 98 | 95 | 50 |
| 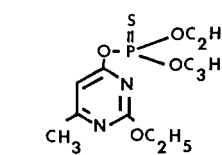 | (42) | 98 | 95 | 95 | 50 |

Table 11-continued (*Meloidogyne incognita* test)

| Active compound | | Degree of destruction in % at an active compound concentration of | | | |
|---|---|---|---|---|---|
| | | 20 | 10 | 5 | 2.5 ppm |

| Structure | No. | 20 | 10 | 5 | 2.5 |
|---|---|---|---|---|---|
| (structure with OCH₃, OC₃H₇, OC₂H₅) | (43) | 100 | 85 | 20 | |
| (structure with OC₂H₅, OC₂H₅, OC₃H₇i) | (52) | 100 | 100 | 100 | 90 |
| (structure with OC₂H₅, NHC₃H₇i, OCH₃) | (14) | 98 | 75 | 50 | |
| (structure with OC₂H₅, NHC₃H₇i, O-CH(CH₃)₂) | (54) | 98 | 90 | | |
| (structure with OC₃H₇, C₂H₅, OC₂H₅) | (48) | 98 | 50 | 50 | |

The process of this invention is illustrated in the following preparative Examples.

EXAMPLE 12 a.

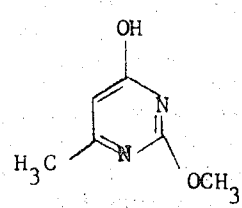

(IIa)

121 g (1.1 moles) of O-methylisourea hydrochloride, followed by 130 g (1 mole) of ethyl acetoacetate were added to a solution of 114 g (2.1 moles) of sodium methylate in 1.2 l of methanol at 5° to 10°C. The mixture was then warmed to 60°C for 15 to 20 minutes, cooled to room temperature and freed from the solvent under reduced pressure. The residue was dissolved in 500 ml of water and concentrated aqueous hydrochloric acid was added to this solution, while cooling, until a pH value of 6 resulted. The precipitate that formed on cooling to 5°C was filtered off.

99 g (71% of theory) of 2-methoxy-4-hydroxy-6-methyl-pyrimidine of melting point 193° to 194°C were obtained.

b.

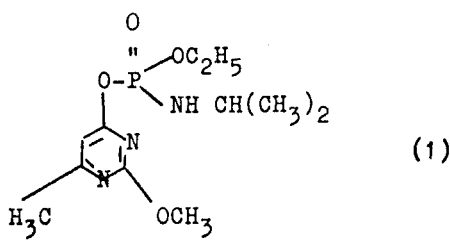

(1)

A mixture of 14 g (0.1 mole) of 2-methoxy-4-hydroxy-6-methyl-pyrimidine and 20.7 g (0.15 mole) of potassium carbonate was suspended in 300 ml of acetonitrile and stirred for 1 hour at 70°C. 15.7 g (0.1 mole) of O-ethyl-N-isopropyl-phosphoric acid ester-amide chloride were added to this mixture at 40° to 50°C and the whole was stirred for 3 hours at the stated temperature. The reaction mixture was then filtered hot, the filtrate was freed from the solvent under reduced pressure and the residue was recrystallized from petroleum ether.

9 g (31% of theory) of O-ethyl-O-[2-methoxy-6-methyl-pyrimidyl-(4)]-N-isopropyl-phosphoric acid ester-amide of melting point 59°C were obtained.

EXAMPLE 13 a.

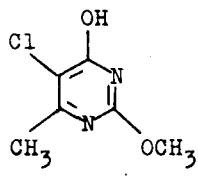

(IIb)

80 g of technical sodium hypochlorite containing about 10% of active chlorine were added at room temperature to a solution of 5 g (0.125 mole) of sodium hydroxide and 14 g (0.1 mole) of 2-methoxy-4hydroxy-6-methyl-pyrimidine in 20 ml of water. After an hour, the mixture was cooled to 10°C and the resulting precipitate was filtered off.

13.3 g (68% of theory) of 2-methoxy-5-chloro-6-methyl-4-pyrimidyloxy-sodium of melting point 197°C were obtained.

b.

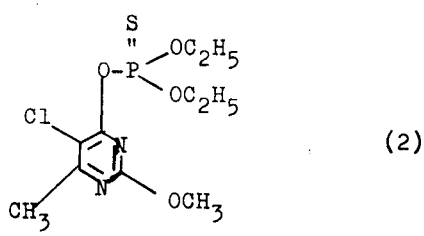

(2)

18.8 g (0.1 mole) of thionophosphoric acid O,O-diethyl ester chloride were added dropwise to a suspension of 20 g (0.1 mole) of 2-methoxy-5-chloro-6-methyl-4-pyrimidyloxy-sodium in 300 ml of acetonitrile at 40° to 50°C. The reaction mixture was stirred at 40° to 50°C for 5 hours and was then cooled to 20°C. After adding 300 ml of toluene and 300 ml of water, the organic phase was separated off, washed with water, dried and freed from the solvent under reduced pressure, and the residue was treated with steam in countercurrent.

22.8 g (70% of theory) of O,O-diethyl-O-[2-methoxy-5-chloro-6-methyl-pyrimidyl-(4)]-thionophosphoric acid ester of refractive index $n_D^{21}$ 1.5148 were obtained.

EXAMPLE 14 a.

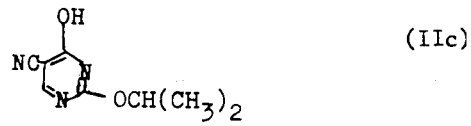

(IIc)

16 g (0.4 mole) of sodium hydroxide, dissolved in 50 ml of water, were added dropwise over the course of one hour to a mixture of 27.7 g (0.2 mole) of isopropylisourea hydrochloride and 33.8 g (0.2 mole) of ethoxymethylenecyanoacetic acid ethyl ester in 100 ml of water at 20°C. The batch was stirred for a further 3 to 5 hours at room temperature and was then acidified with dilute hydrochloric acid until a precipitate was formed. The latter was filtered off and recrystallized from a little methanol.

11 g (58% of theory) of 2-isopropoxy-4-hydroxy-5-cyano-pyrimidine of melting point 166°C were obtained.

b.

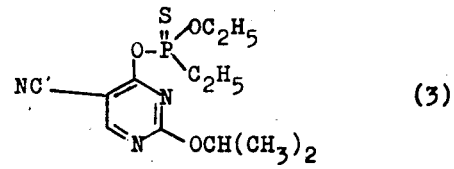

(3)

17.4 g (0.1 mole) of O-ethyl-ethanethionophosphonic acid ester chloride were added dropwise at room temperature to a mixture of 17.9 g (0.1 mole) of 2-isopropoxy-4-hydroxy-5-cyano-pyrimidine and 14.3 g (0.11 mole) of potassium carbonate in 200 ml of acetonitrile. The mixture was then stirred for a further 3 hours, at 40°C. The potassium chloride which had separated out was then filtered off. 500 ml of toluene and 200 ml of saturated sodium bicarbonate solution were added to the filtrate. The organic phase was separated off and washed with water; after drying over sodium sulfate, the solvent was removed and the residue was purified by "slight distillation".

25.5 g (80% of theory) of O-ethyl-O-[2-isopropoxy-5-cyano-pyrimidyl-(4)]-ethanethionophosphonic acid ester of refractive index $n_D^{23}$ 1.5272 were obtained.

The intermediates listed in Table 12 which follows could be prepared by counterparts of the methods described in Examples 12(a), 13(a) and 14(a) and used to make the end products set forth in Table 13 by the method of Examples 12(b), 13 (b) and 14(b).

Table 12

$$\underset{R^3}{\overset{R^2}{\diagdown}}\underset{N}{\overset{OH}{\diagdown}}\underset{OR^1}{\overset{N}{\diagdown}} \quad (II)$$

| Intermediate No. II | R¹ | R² | R³ | Melting point [°C] |
|---|---|---|---|---|
| (d) | C₂H₅ | H | CH₃ | 187 |
| (e) | CH₃ | H | CH₂COOCH₃ | 138 |
| (f) | CH₃ | COCH₃ | H | 140 |
| (g) | CH₃ | Br | CH₃ | 163 |
| (h) | CH₃ | CH₃ | CH₃ | 168 |
| (i) | CH₃ | C₂H₅ | CH₃ | 210 |
| (j) | CH₃ | SCH₃ | CH₃ | 159 |
| (k) | CH(CH₃)₂ | H | CH₃ | 139 |
| (l) | CH(CH₃)₂ | H | CH₂COOCH₃ | 114 |
| (m) | CH(CH₃)₂ | Br | CH₃ | 138 |
| (n) | CH(CH₃)₂ | CH₃ | CH₃ | 138 |
| (o) | CH(CH₃)₂ | —(CH₂)₃— | | 182 |
| (p) | CH(CH₃)₂ | H |  | 177 |
| (q) | CH(CH₃)₂ | SCH₃ | CH₃ | 123 |
| (r) | CH(CH₃)₂ | COCH₃ | H | 136 |
| (s) | CH(CH₃)₂ | Cl | CH₃ | 153 |
| (t) | (CH₂)₁₁CH₃ | H | CH₃ | 64 |
| (u) |  | H | CH₃ | 10 |
| (v) |  | Cl | CH₃ | 129 |
| (w) |  | —(CH₂)₃— | | 148 |
| (x) | CH₂—CH=CH₂ | H | CH₃ | 170 |
| (y) | CH₂—C≡CH | H | CH₃ | 183 |
| (z) | C₂H₅ | OC₂H₅ | H | 149 |
| (aa) | C₂H₅ | COOC₂H₅ | H | 150 |
| (bb) |  | H | CH₃ | 148 |

Table 13

$$\underset{R^3}{\overset{R^2}{\diagdown}}\underset{N}{\overset{O-P\diagup R^5}{\diagdown}}\underset{OR^1}{\overset{N}{\diagdown}} \quad (I)$$

| Compound No. | R¹ | R² | R³ | R⁴ | R⁵ | X | Refractive index |
|---|---|---|---|---|---|---|---|
| 4 | CH₃ | H | CH₃ | C₂H₅ | OC₂H₅ | S | $n_D^{22}$ 1.5012 |
| 5 | CH₃ | H | CH₃ | CH₃ | C₂H₅ | S | $n_D^{21}$ 1.5282 |
| 6 | CH₃ | H | CH₃ | CH₃ | OCH₃ | S | $n_D^{23}$ 1.5200 |
| 7 | CH₃ | H | CH₃ | C₂H₅ | SC₃H₇ | S | $n_D^{23}$ 1.5415 |
| 8 | CH₃ | H | CH₃ | C₂H₄OC₂H₅ | | S | $n_D^{23}$ 1.5024 |
| 9 | CH₃ | H | CH₃ | C₂H₅ | OC₃H₇ | S | $n_D^{24}$ 1.5028 |
| 10 | CH₃ | H | CH₃ | CH₃ | OC₃H₇ | S | $n_D^{24}$ 1.5103 |
| 11 | CH₃ | H | CH₃ | C₃H₇ | C₂H₅ | S | $n_D^{23}$ 1.5169 |
| 12 | CH₃ | H | CH₃ | C₂H₅ | OC₂H₅ | O | $n_D^{22}$ 1.4782 |
| 13 | CH₃ | H | CH₃ | C₂H₅ | C₂H₅ | S | $n_D^{22}$ 1.5202 |
| 14 | CH₃ | H | CH₃ | C₂H₅ | NHCH(CH₃)₂ | S | $n_D^{23}$ 1.5168 |
| 15 | CH₃ | H | CH₃ | C₂H₅ | C₆H₅ | S | $n_D^{23}$ 1.5705 |
| 16 | CH₃ | H | CH₂COOCH₃ | C₃H₇ | C₂H₅ | S | $n_D^{21}$ 1.5123 |
| 17 | CH₃ | H | CH₂COOCH₃ | C₂H₅ | C₆H₅ | S | $n_D^{21}$ 1.5520 |
| 18 | CH₃ | H | CH₂COOCH₃ | C₂H₅ | OC₂H₅ | O | $n_D^{21}$ 1.4826 |
| 19 | CH₃ | H | CH₂COOCH₃ | C₂H₅ | OC₂H₅ | S | $n_D^{21}$ 1.5050 |
| 20 | CH₃ | COCH₃ | H | C₂H₅ | C₂H₅ | S | $n_D^{21}$ 1.5400 |
| 21 | CH₃ | COCH₃ | H | CH₃ | C₂H₅ | S | $n_D^{21}$ 1.5479 |
| 22 | CH₃ | CH₃ | CH₃ | C₂H₅ | OC₂H₅ | S | $n_D^{23}$ 1.5067 |
| 23 | CH₃ | Br | CH₃ | C₂H₅ | OC₃H₇ | S | $n_D^{21}$ 1.5297 |
| 24 | CH₃ | Br | CH₃ | CH₃ | C₂H₅ | S | $n_D^{21}$ 1.5484 |

Table 13-continued

Structure (I):
$$\begin{array}{c} X \\ \| \\ R^2O-P(OR^4)(R^5) \end{array}$$
attached to pyrimidine with $R^2, R^3, OR^1$ substituents

| Compound No. | $R^1$ | $R^2$ | $R^3$ | $R^4$ | $R^5$ | X | Refractive index |
|---|---|---|---|---|---|---|---|
| 25 | $C_3$ | Br | $CH_3$ | $C_2H_5$ | $C_2H_5$ | S | $n_D^{21}$ 1.5402 |
| 26 | $CH_3$ | Br | $CH_3$ | $C_2H_5$ | $C_6H_5$ | S | $n_D^{22}$ 1.5825 |
| 27 | $CH_3$ | Br | $CH_3$ | $C_2H_5$ | $OC_2H_5$ | S | $n_D^{23}$ 1.5181 |
| 28 | $CH_3$ | Cl | $CH_3$ | $CH_3$ | $OC_3H_7$ | S | $n_D^{21}$ 1.5178 |
| 29 | $CH_3$ | Cl | $CH_3$ | $CH_3$ | $C_2H_5$ | S | $n_D^{21}$ 1.5394 |
| 30 | $CH_3$ | Cl | $CH_3$ | $C_3H_7$ | $C_2H_5$ | S | $n_D^{21}$ 1.5280 |
| 31 | $CH_3$ | Cl | $CH_3$ | $C_2H_5$ | $C_6H_5$ | S | $n_D^{21}$ 1.5752 |
| 32 | $CH_3$ | Cl | $CH_3$ | $C_2H_5$ | $OC_3H_7$ | S | $n_D^{21}$ 1.5224 |
| 33 | $CH_3$ | Cl | $CH_3$ | $C_2H_5$ | $OC_2H_5$ | S | $n_D^{22}$ 1.5196 |
| 34 | $CH_3$ | $SCH_3$ | $CH_3$ | $C_2H_5$ | $C_2H_5$ | S | $n_D^{22}$ 1.5367 |
| 35 | $CH_3$ | $SCH_3$ | $CH_3$ | $C_2H_5$ | $OC_3H_7$ | S | $n_D^{22}$ 1.5210 |
| 36 | $CH_3$ | $SCH_3$ | $CH_3$ | $C_2H_5$ | $SC_3H_7$ | S | $n_D^{22}$ 1.5553 |
| 37 | $CH_3$ | $SCH_3$ | $CH_3$ | $C_2H_5$ | $C_6H_5$ | S | $n_D^{23}$ 1.5832 |
| 38 | $CH_3$ | $SCH_3$ | $CH_3$ | $C_2H_5$ | $OC_2H_5$ | O | $n_D^{24}$ 1.5082 |
| 39 | $CH_3$ | $SCH_3$ | $CH_3$ | $C_2H_5$ | $NHC_3H_7i$ | S | $n_D^{22}$ 1.5342 |
| 40 | $C_2H_5$ | H | $CH_3$ | $CH_3$ | $OCH_3$ | S | $n_D^{20}$ 1.5300 |
| 41 | $C_2H_5$ | H | $CH_3$ | $C_2H_5$ | $OC_2H_5$ | S | $n_D^{20}$ 1.5033 |
| 42 | $C_2H_5$ | H | $CH_3$ | $C_2H_5$ | $OC_3H_7$ | S | $n_D^{21}$ 1.4975 |
| 43 | $C_2H_5$ | H | $CH_3$ | $CH_3$ | $OC_3H_7$ | S | $n_D^{21}$ 1.5058 |
| 44 | $C_2H_5$ | H | $CH_3$ | $CH_3$ | $C_2H_5$ | S | $n_D^{21}$ 1.5242 |
| 45 | $C_2H_5$ | H | $CH_3$ | $C_2H_4OC_2H_5$ | $OC_2H_5$ | S | $n_D^{24}$ 1.4973 |
| 46 | $C_2H_5$ | H | $CH_3$ | $C_2H_5$ | $C_6H_5$ | S | $n_D^{23}$ 1.5619 |
| 47 | $C_2H_5$ | H | $CH_3$ | $C_2H_5$ | $C_2H_5$ | S | $n_D^{22}$ 1.5127 |
| 48 | $C_2H_5$ | H | $CH_3$ | $C_3H_7$ | $C_2H_5$ | S | $n_D^{23}$ 1.5098 |
| 49 | $CH(CH_3)_2$ | H | $CH_3$ | $CH_3$ | $OC_3H_7$ | S | $n_D^{20}$ 1.5080 |
| (50) | $CH(CH_3)_2$ | H | $CH_3$ | $CH_3$ | $OCH_3$ | S | $n_D^{20}$ 1.5240 |
| 51 | $CH(CH_3)_2$ | H | $CH_3$ | $C_2H_5$ | $OC_3H_7$ | S | $n_D^{22}$ 1.4970 |
| 52 | $CH(CH_3)_2$ | H | $CH_3$ | $C_2H_5$ | $OC_2H_5$ | S | $n_D^{22}$ 1.4995 |
| 53 | $CH(CH_3)_2$ | H | $CH_3$ | $CH_3$ | $C_2H_5$ | S | $n_D^{23}$ 1.5160 |
| 54 | $CH(CH_3)_2$ | H | $CH_3$ | $C_2H_5$ | $NHCH(CH_3)_2$ | S | $n_D^{23}$ 1.5065 |
| 55 | $CH(CH_3)_2$ | H | $CH_3$ | $C_2H_5$ | $C_6H_5$ | S | $n_D^{23}$ 1.5538 |
| 56 | $CH(CH_3)_2$ | H | $CH_3$ | $C_2H_5$ | $C_2H_5$ | S | $n_D^{22}$ 1.5098 |
| 57 | $CH(CH_3)_2$ | H | $CH_3$ | $C_2H_5$ | $OC_2H_5$ | O | $n_D^{23}$ 1.4812 |
| 58 | $CH(CH_3)_2$ | H | $CH_3$ | $C_3H_7$ | $C_2H_5$ | S | $n_D^{23}$ 1.5057 |
| 59 | $CH(CH_3)_2$ | H | $CH_3$ | $C_2H_5$ | $SC_3H_7$ | S | $n_D^{23}$ 1.5355 |
| 60 | $CH(CH_3)_2$ | H | $CH_3$ | $C_2H_5$ | $NHCH(CH_3)_2$ | O | $n_D^{22}$ 1.4708 |
| 61 | $CH(CH_3)_2$ | H | $C_6H_5$ | $C_2H_5$ | $OC_2H_5$ | S | $n_D^{24}$ 1.5520 |
| 62 | $CH(CH_3)_2$ | H | $C_6H_5$ | $C_2H_5$ | $C_2H_5$ | S | $n_D^{24}$ 1.5572 |
| 63 | $CH(CH_3)_2$ | H | $C_6H_5$ | $C_2H_5$ | $C_6H_5$ | S | $n_D^{24}$ 1.5899 |
| 64 | $CH(CH_3)_2$ | H | $CH_2COOCH_3$ | $C_2H_5$ | $C_6H_5$ | S | $n_D^{21}$ 1.5503 |
| 65 | $CH(CH_3)_2$ | H | $CH_2COOCH_3$ | $C_2H_5$ | $C_2H_5$ | S | $n_D^{21}$ 1.5115 |
| 66 | $CH(CH_3)_2$ | H | $CH_2COOCH_3$ | $C_3H_7$ | $C_2H_5$ | S | $n_D^{21}$ 1.5100 |
| 67 | $CH(CH_3)_2$ | H | $CH_2COOCH_3$ | $C_2H_5$ | $OC_2H_5$ | S | $n_D^{22}$ 1.4995 |
| 68 | $CH(CH_3)_2$ | H | $CH_2COOCH_3$ | $CH_3$ | $C_2H_5$ | S | $n_D^{22}$ 1.5182 |
| 69 | $CH(CH_3)_2$ | CN | H | $CH_3$ | $C_2H_5$ | S | $n_D^{21}$ 1.5327 |
| 70 | $CH(CH_3)_2$ | CN | H | $C_2H_5$ | $OC_2H_5$ | S | $n_D^{21}$ 1.5119 |
| 71 | $CH(CH_3)_2$ | CN | H | $C_2H_5$ | $OC_3H_7$ | S | $n_D^{22}$ 1.5150 |
| 72 | $CH(CH_3)_2$ | CN | H | $C_3H_7$ | $C_2H_5$ | S | $n_D^{22}$ 1.5202 |
| 73 | $CH(CH_3)_2$ | CN | H | $C_2H_5$ | $C_6H_5$ | S | semi-crystalline |
| 74 | $CH(CH_3)_2$ | CN | H | $C_2H_5$ | $SC_3H_7$ | S | $n_D^{21}$ 1.5362 |
| 75 | $CH(CH_3)_2$ | $COCH_3$ | H | $C_2H_5$ | $OC_2H_5$ | S | $n_D^{21}$ 1.5072 |
| 76 | $CH(CH_3)_2$ | $COCH_3$ | H | $C_2H_5$ | $C_2H_5$ | S | $n_D^{22}$ 1.5068 |
| 77 | $CH(CH_3)_2$ | $COCH_3$ | H | $C_3H_7$ | $C_2H_5$ | S | $n_D^{21}$ 1.5181 |
| 78 | $CH(CH_3)_2$ | $CH_3$ | $CH_3$ | $C_2H_5$ | $OC_2H_5$ | S | $n_D^{22}$ 1.5018 |
| 79 | $CH(CH_3)_2$ | Cl | $CH_3$ | $C_2H_5$ | $OC_2H_5$ | S | $n_D^{20}$ 1.5055 |
| 80 | $CH(CH_3)_2$ | Cl | $CH_3$ | $CH_3$ | $C_2H_5$ | S | $n_D^{20}$ 1.5258 |
| 81 | $CH(CH_3)_2$ | Cl | $CH_3$ | $C_3H_7$ | $C_2H_5$ | S | $n_D^{21}$ 1.5165 |
| 82 | $CH(CH_3)_2$ | Cl | $CH_3$ | $CH_3$ | $OC_3H_7$ | S | $n_D^{21}$ 1.5112 |
| 83 | $CH(C_3)_2$ | Cl | $CH_3$ | $C_2H_5$ | $OC_3H_7$ | S | $n_D^{21}$ 1.5059 |
| 84 | $CH(CH_3)_2$ | Cl | $CH_3$ | $C_2H_5$ | $OC_2H_5$ | O | $n_D^{21}$ 1.4818 |
| 85 | $CH(CH_3)_2$ | Cl | $CH_3$ | $C_2H_5$ | $C_6H_5$ | S | $n_D^{21}$ 1.5601 |
| 86 | $CH(CH_3)_2$ | Cl | $CH_3$ | $C_2H_5$ | $SC_3H_7$ | S | $n_D^{21}$ 1.5350 |
| 87 | $CH(CH_3)_2$ | $SCH_3$ | $CH_3$ | $C_2H_5$ | $C_2H_5$ | S | $n_D^{23}$ 1.5273 |
| 88 | $CH(CH_3)_2$ | $SCH_3$ | $CH_3$ | $C_2H_5$ | $OC_2H_5$ | S | $n_D^{23}$ 1.5160 |
| 89 | $CH(CH_3)_2$ | $SCH_3$ | $CH_3$ | $C_2H_5$ | $OC_3H_7$ | S | $n_D^{23}$ 1.5112 |
| 90 | $CH(CH_3)_2$ | $SCH_3$ | $CH_3$ | $C_2H_5$ | $SC_3H_7$ | S | $n_D^{23}$ 1.5371 |
| 91 | $CH(CH_3)_2$ | $SCH_3$ | $CH_3$ | $C_2H_5$ | $C_6H_5$ | S | $n_D^{23}$ 1.5700 |
| 92 | $CH(CH_3)_2$ | $SCH_3$ | $CH_3$ | $C_2H_5$ | $NHC_3H_7i$ | S | $n_D^{23}$ 1.5272 |
| 93 | $CH(CH_3)_2$ | $SCH_3$ | $CH_3$ | $C_2H_5$ | $OC_2H_5$ | O | $n_D^{22}$ 1.5060 |
| 94 | $CH(CH_3)_2$ | $-(CH_2)_3-$ | | $C_2H_5$ | $OC_2H_5$ | S | $n_D^{22}$ 1.5149 |
| 95 | $CH(CH_3)_2$ | $-(CH_2)_3-$ | | $C_2H_5$ | $C_2H_5$ | S | $n_D^{22}$ 1.5257 |
| 96 | $CH_2C\equiv CH$ | H | $CH_3$ | $CH_3$ | $C_2H_5$ | S | $n_D^{21}$ 1.5507 |
| 97 | $CH_2C\equiv CH$ | H | $CH_3$ | $C_2H_5$ | $OC_2H_5$ | S | $n_D^{21}$ 1.5248 |
| 98 | $CH_2CH=CH_2$ | H | $CH_3$ | $C_2H_5$ | $OC_2H_5$ | S | $n_D^{24}$ 1.5127 |
| 99 | $CH_2CH=CH_2$ | H | $CH_3$ | $C_3H_7$ | $C_2H_5$ | S | $n_D^{24}$ 1.5214 |
| 100 | $CH_2CH=CH_2$ | H | $CH_3$ | $CH_3$ | $C_2H_5$ | S | $n_D^{24}$ 1.5312 |
| 101 | $CH_2CH=CH_2$ | H | $CH_3$ | $C_2H_5$ | $C_6H_5$ | S | $n_D^{24}$ 1.5678 |
| 102 | $C_6H_{11}$ | H | $CH_3$ | $C_2H_5$ | $OC_2H_5$ | S | $n_D^{22}$ 1.5148 |

Table 13-continued

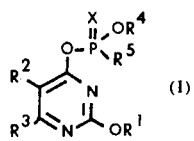

(1)

| Compound No. | R¹ | R² | R³ | R⁴ | R⁵ | X | Refractive index |
|---|---|---|---|---|---|---|---|
| 103 | ⟨H⟩— | Cl | CH₃ | C₂H₅ | OC₂H₅ | S | $n_D^{23}$ 1.5162 |
| 104 | ⟨H⟩— | —(CH₂)₃— | | C₂H₅ | OC₂H₅ | S | $n_D^{22}$ 1.5250 |
| 105 | (CH₂)₁₁CH₃ | H | CH₃ | C₂H₅ | OC₂H₅ | S | $n_D^{23}$ 1.4770 |
| 106 | C₂H₅ | OC₂H₅ | H | C₂H₅ | OC₂H₅ | S | $n_D^{20}$ 1.5049 |
| 107 | C₂H₅ | COOC₂H₅ | H | C₂H₅ | OC₂H₅ | S | $n_D^{26}$ 1.5044 |
| 108 | C₂H₅ | COOC₂H₅ | H | CH₃ | C₂H₅ | S | $n_D^{26}$ 1.5239 |
| 109 | CH₂—⟨⟩ | H | CH₃ | C₂H₅ | OC₂H₅ | S | $n_D^{23}$ 1.5435 |

It will be appreciated that the instant specification and examples are set forth by way of illustration and not limitation, and that various modifications and changes may be made without departing from the spirit and scope of the present invention.

What is claimed is:

1. A pyrimidin(4)-yl-(thiono)-(thiol)-phosphoric-(phosphonic) acid ester or ester-amide of the formula

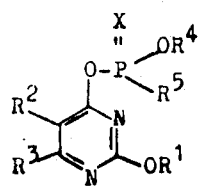

in which $R^1$ is straight-chain or branched alkyl with 1 to 20 carbon atoms, cycloalkyl with 5 to 7 carbon atoms, alkenyl or alkynyl with 2 to 6 carbon atoms or aralkyl with 6 to 10 carbon atoms in the aryl moiety and 1 to 2 carbon atoms in the alkyl moiety, $R^2$ is hydrogen, straight-chain or branched alkyl with 1 to 4 carbon atoms, alkoxy with 1 to 4 carbon atoms, alkylmercapto with 1 to 4 carbon atoms, alkylcarbonyl or alkoxycarbonyl with 1 to 4 carbon atoms in the alkyl or alkoxy moiety, halogen or nitrile, $R^3$ is hydrogen, straight-chain or branched alkyl with 1 to 6 carbon atoms, or alkoxycarbonylalkyl with 1 to 4 carbon atoms in the alkoxy radical and 1 to 2 carbon atoms in the alkyl radical, or $R^2$ and $R^3$ conjointly form an alkylene bridge which forms a 5-membered to 7-membered ring with the adjoining carbon atoms, $R^4$ is straight-chain or branched alkyl with 1 to 12 carbon atoms or alkoxyalkyl with 1 to 12 carbon atoms in the alkyl radical and 1 to 4 carbon atoms in the alkoxy radical, $R^5$ is straight-chain or branched alkyl, alkoxy or alkylmercapto with 1 to 6 carbon atoms or aryl with 6 to 10 carbon atoms, and X is oxygen or sulfur 2. The compound according to claim 1 wherein such compound is O-methyl-O-[2-methoxy-6-methyl-pyrimidyl-(4)]-ethanethionophosphonic acid ester of the formula

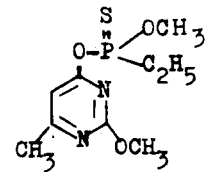

3. The compound according to claim 1 wherein such compound is O-methyl-O-[2-ethoxy-6-methyl-pyrimidyl-(4)]-ethanethionophosphonic acid ester of the formula

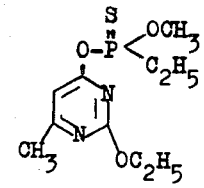

* * * * *